(12) United States Patent
Donnelly et al.

(10) Patent No.: US 7,606,721 B1
(45) Date of Patent: Oct. 20, 2009

(54) PATIENT CREDIT BALANCE ACCOUNT ANALYSIS, OVERPAYMENT REPORTING AND RECOVERY TOOLS

(75) Inventors: Patrick J. Donnelly, Eldersburg, MD (US); Jeffrey R. Donnelly, Cockeysville, MD (US)

(73) Assignee: CDR Associates, LLC, Timonium, MD (US)

( * ) Notice: Subject to any disclaimer, the term of this patent is extended or adjusted under 35 U.S.C. 154(b) by 1051 days.

(21) Appl. No.: 10/356,094

(22) Filed: Jan. 31, 2003

(51) Int. Cl.
*G06Q 50/00* (2006.01)
*G06Q 40/00* (2006.01)

(52) U.S. Cl. .................................. 705/2; 705/30; 705/40

(58) Field of Classification Search ................... 705/2.3, 705/35
See application file for complete search history.

(56) References Cited

U.S. PATENT DOCUMENTS

| | | | |
|---|---|---|---|
| 5,235,702 A * | 8/1993 | Miller | 707/102 |
| 5,359,509 A * | 10/1994 | Little et al. | 705/2 |
| 5,704,044 A * | 12/1997 | Tarter et al. | 705/4 |
| 5,956,690 A * | 9/1999 | Haggerson et al. | 705/3 |
| 5,991,733 A | 11/1999 | Aleia et al. | |
| 6,073,104 A | 6/2000 | Field | |
| 6,341,265 B1 | 1/2002 | Provost et al. | |
| 6,343,271 B1 | 1/2002 | Peterson et al. | |
| 2001/0027403 A1 | 10/2001 | Peterson et al. | |
| 2002/0026328 A1 | 2/2002 | Westerkamp et al. | |

FOREIGN PATENT DOCUMENTS

| | | |
|---|---|---|
| JP | 60229234 | 4/1987 |
| WO | WO0067168 | 11/2000 |

OTHER PUBLICATIONS

Anonymous "Credit Balances: Spotlighting a Little-Known Area of Risk and Opportunity," Jan. 2004, Healthcare Financial Management, vol. 58, No. 1, S1.*
IBM Technical Disclosure Bulletin, vol. 29 No. 2, Jul. 1986, USA, Four Pages Cover Page, Page With Copy Right Notice, And pp. 855-856.
James E. Massey, entitled: "Formula for Analyzing Accounts Receivable Management Performance", Topics and Presentations, Sep. 20, 2002, pp. 1-3.

* cited by examiner

*Primary Examiner*—C. Luke Gilligan
*Assistant Examiner*—R. L. Porter
(74) *Attorney, Agent, or Firm*—Volpe and Koenig, P.C.

(57) ABSTRACT

The present invention provides a system for managing, analyzing and reporting accounts of overpaid claims for patient balance accounts, although various components and features of the system are inventions into themselves. Certain aspects of the inventor allow managers of both service providers (such as health care facilities) and payers (such as insurance companies and Medicare) to assign work and produce reports. Other aspects of the invention allow provider users and payer users to analyze and resolve the claims in an automated environment. These aspects provide the users with information in a readily accessible and easy to navigate format. The users are also provided with tools for analyzing the claims in an automated manner.

60 Claims, 35 Drawing Sheets

FIG. 4

Auditing System

View Accounts

Payments | Audit History | Demographics | Insurance Information | Notes | Possible Related Accounts

Patient Information

Patient Name  ADAMS, ROBERT — 104
Account Number  F0789288 — 106
SSN  XXX-XX-XXXX — 108

DOB  XX/XX/XX — 110
Marital Status  S — 112
Admit Date  05/23/02 — 114

Guarantor Information

Guarantor Name  ADAMS, ROBERT — 116
Guarantor Address  XX ABC Street
Baltimore City, MD XXXXX — 118

HOME website . contact us . help

— 102

Auditing System

View Accounts

Payments | Audit History | Demographics | Insurance Information | Notes | Possible Related Accounts ALLEN, STEPHNEY Account Number: F0385924

| Post Date | Service Date | Note |
|---|---|---|
| 08/11/99 | 08/11/99 | PT PRESENTED TO THE ER FOR TREATMENT, PT HAS KAISER PERMANENTE. A COPY OF THE CARD ALONG WITH HER ID WERE PLACED WITH THE ER CHART. 9:30 A.M. |
| 08/18/99 | 08/18/99 | SENT ACCOUNT TO KAISER PERMANENTE WITH ER REPORT. |
| 09/08/99 | 09/08/99 | LAWYER REQUESTED BILLING INFORMATION THE YOST LEGAL GROUP XXXN ABCD ST BALTIMORE, MD XXXXX (XXX)XXX-XXXX |
| 01/21/00 | 01/21/00 | SENT CLAIM TO INSURANCE CO. |
| 09/11/00 | 09/11/00 | CALLED KAISER AND TT GLENDALE...SHE SD THT CLM DENIED ON 9/30/99 FOR MED RECS. ASKED HER FOR CLM#... SHE GAVE ME CLM#5734989.. REQTD UB |
| 09/14/00 | 09/14/00 | TO BILL W/MED RECS AND CLM#. |
| 11/13/00 | 11/13/00 | REC'V UB WAITING ON MEDRECS |
|  |  | REC'V MED RECS BILLED KAISER |
| 01/09/01 | 01/09/01 | CALLED KAISER AND TT SHONTAY... SHE SD THT PYMT WAS ISSUED ON 12/11/00 FOR $108.70 AND PT IS RESP FOR $70.00. |

HOME website. contact us. help

Auditing System

HOME website . contact us . help

View Accounts

Payments | Audit History | Demographics | Insurance Information | Notes | Possible Related Accounts ADAMS, ROBERT Account Number: F0768385

| Account Number | Patient Name | Admit Date | Discharge Date | Total Charges | Balance |
|---|---|---|---|---|---|
| F0766426 ~1461 | xxxxxx ~1481 | 03/14/02 ~1501 | 01/01/00 ~1521 | $0.00 ~1541 | ($88.48) ~1561 |
| F0768385 ~1462 | xxxxxx ~1482 | 03/14/02 ~1502 | 01/01/00 ~1522 | $0.00 ~1542 | ($91.68) ~1562 |
| F0772308 ~1463 | xxxxxx ~1483 | 03/14/02 ~1503 | 01/01/00 ~1523 | $0.00 ~1543 | $32.93 ~1563 |
| F0789288 ~1464 | xxxxxx ~1484 | 03/14/02 ~1504 | 01/01/00 ~1524 | $0.00 ~1544 | ($131.74) ~1564 |
| F0800780 ~1465 | xxxxxx ~1485 | 03/14/02 ~1505 | 01/01/00 ~1525 | $0.00 ~1545 | ($227.58) ~1565 |
| F0806070 ~1466 | xxxxxx ~1486 | 03/14/02 ~1506 | 01/01/00 ~1526 | $0.00 ~1546 | ($932.15) ~1566 |
| F0819866 ~1467 | xxxxxx ~1487 | 03/14/02 ~1507 | 01/01/00 ~1527 | $0.00 ~1547 | $32.93 ~1567 |
| F0827082 ~1468 | xxxxxx ~1488 | 03/14/02 ~1508 | 01/01/00 ~1528 | $0.00 ~1548 | $164.67 ~1568 |

144

Auditing System

View Accounts

HOME website . contact us . help

Payments  Audit History  Demographics  Insurance Information  Notes  Possible Related Accounts ADAMS, ROBERT Account Number: F0800780

| Type | Date Posted | Amount | Service Code | Adjustment Reason | Posted By |
|---|---|---|---|---|---|
| T — 162₁ | 09/17/02 | $267.40 — 164₁ | PBCMD-RCP — 166₁ | Transfer To F0827082 — 168₁ | CDR Associates — 172₁ — 170₁ |
| R — 162₂ | 10/14/02 | $267.40 — 164₂ | PBCMD-RCP — 166₂ | Refund MEDICARE PART A AND B — 168₂ — 170₂ | CDR Associates — 172₂ |
| R — 162₃ | 10/14/02 | $267.40 — 164₃ | PBCMD-RCP — 166₃ | Refund BLUE CROSS OF MARYLAND — 168₃ — 170₃ | CDR Associates — 172₃ |

[ Print Letter ]  [ Print Form ]  [ Show Refund ]
    176            178           180

PATIENT FINANCIAL SERVICES
EXPLANATION OF BENEFITS REQUEST FORM

REQUESTOR NAME Pete Teta sysadmin — 182, 186
DATE 10/21/02 — 184

190

| PATIENT NAME | ACCOUNT NUMBER | DESCRIPTION | PAYMENT DATE | PAYMENT AMOUNT |
|---|---|---|---|---|
| ANDERSON, NELLIE L | 900112989-0 | MEDICARE ELECTRONIC PAYMEN | 08/01/00 | ($233.56) |

188 — 192 — 194

COMMENTS:
— 196

FIG. 10

_____ Associates, LLC.                                    Monday, October 21, 2002

Maryland General Hospital
                            Refund Worksheet

Patients Name:    XXXXXXXXX ─186        Payable To:  ╱202  BLUE CROSS OF MARYLAN
Account Number:   F0475383 ──188        Address: 204╱     XXXXX MILL RUN CIRCLE
Facility:                  ──196                    206╲  OWNGS MILLS, MD XXXXX
Date of Service:  4/28/2000──198        Prepared By: _____ Associates, LLC.
Refund Amount:    $187.82 ──200

| DATE | DESC | PYMTAMT |
|------|----------|-----------|
| 5/11/2000 | PBCMD-RCP | ($573.56) |
| 5/11/2000 | ABCMD-ADJ | ($36.61) |

208

Total Charges:         $410.36
Total Payments:       ($573.56)
Total Allowances:      ($36.61)
                      ─────────
Subtotal:             ($199.81)
Allowance Adjustment:   $11.99
Balance Transfers:       $0.00
Total Refunds:         $187.82

─210

Explanation:  Credit adjustment to charges after original billing.
              ╲
              212

December 19, 2002

[ Payable to Field ] —— 202

[ Payable Address Field ] —— 204

To Whom It May Concern: Enclosed is a refund check in the amount of $31.30. This refund has been issued on a claim for ____. The reason for the refund and the specific details are identified below.

DOS          08/30/02
Policy Number   000-00-0000
Group Number
Subscriber
COB Insurance
COB Subscriber
Explanation     Patient Overpayment. Patient is only responsible for total charges of $48.70.

If you have any questions, please contact me at (410) 560-XXXX

Sincerely,

Pete Teta sysadmin

Auditing System

View Accounts

| Payments | Audit Histo |
|---|---|

ALEXANDER, JUSTIN

Calculator

Total Charges  $504.1

| Summary | Primar | MEDIC |
|---|---|---|

| Insurance | | |
|---|---|---|
| Responsibility | 504.14 | |
| Expected Payment | 504.14 | |
| Expected Adjustment | 0.00 | |
| Actual Payment | 504.14 | |
| Actual Adjustment | 0.00 | |
| Refund Amount | 0.00 | |
| Adjustment Amount | 0.00 | |

[Verify Data] [Reset] [Draft] [Save] [Cancel]

---

Auditing System: Account Details - Calculator - Microsoft Internet E...

View Accounts

ALEXANDER, JUSTINE I  Account Number: 900175191-7

Payment/Adjustment Summary

| Service Code | Description | Total |
|---|---|---|

Payments ~278

| ☐ 288₁ 00100297 | 282₁ BLUE CROSS PAYMENT 284₁ | 286₁ ($155.88) |
| ☐ 288₂ 00800193 | 282₂ MC ELECTRONIC WD 284₂ | 286₂ $321.62 |
| ☐ 288₃ 09000191 | 282₃ MEDICARE ELECTRONIC PAYMEN 284₃ | 286₃ ($814.04) |

Adjustments ~280

| ☐ 288₄ 00200196 | 282₄ MEDICARE ALLOWANCE 284₄ | 286₄ $0.00 |
| ☐ 288₅ 00200295 | 282₅ BLUE CROSS ALLOWANCE 284₅ | 286₅ ($3.18) |
| ☐ 288₆ 00700211 | 282₆ MEDICARE ABN - DENIAL 284₆ | 286₆ ($11.72) |

290 — [OK] [Cancel]

Auditing System: Account Details - Calculator - Microsoft Internet Explorer

View Accounts

Account Number: 248

Calculate Percentage       Current Percentage  100.0 %

300    296                    294
       Payments 292                           Adjustments 295

○ MEDICARE ELECTRONIC PAYMEN    ($9,035.38)    ○ MEDICARE ALLOWANCE    ($627.29)
○ MEDICARE ELECTRONIC PAYMEN    ($8,406.38)    ○ MEDICARE ALLOWANCE    ($587.14)
○ MEDICARE ELECTRONIC PAYMEN    ($7,234.27)    ○ MEDICARE ALLOWANCE    ($512.32)
○ BLUE CROSS PAYMENT            ($792.00)     ○ MEDICARE ALLOWANCE    $512.32
○ MC ELECTRONIC WD              $7,234.27     ○ MEDICARE ALLOWANCE    $627.29
○ MC ELECTRONIC WD              $9,035.38

302 —  [ OK ]   [ Reset ]   [ Cancel ]

| Auditing System: Account Details - Post Refund - Microsoft Internet Explorer |

View Accounts

Account Number:

Total Charges $7.50    Account Balance Balance ($32.27)    Audited Balance ($32.27)

Refund Information

| Field | Value |
|---|---|
| From DOS | 08/07/02 |
| To DOS | 08/07/02 |
| Claim Charges | $7.50 |
| Insurance | MEDICARE PART A AND B |
| Refund Amount | $24.77 |
| COB Insurance | MEDICARE PART A AND B |
| ICN Number | MEDICARE PART A AND B |
| Note Reference | Working Aged - Medicare is Primary |
| Explanation | Working Aged - Medicare is Primary. ESRD - Patient has completed the coordination period, Medicare is primary. |

Click to select an explanation:

Duplicate Payment
EGHP coverage is primary.
ESRD - Patient has completed the coordination period, Medicare is primary.
ESRD - Patient is still in the coordination period, Medicare is secondary.
LGHP coverage is primary, Medicare is secondary.

Validation Source
☑ Based on System Data
☐ Called Insurer/Insurer's System
☐ Called Patient

[ OK ]  [ Reset ]  [ Cancel ]

Auditing System

View Accounts

HOME website . contact us . help

Payments | Audit History | Demographics | Insurance Information | Notes | Possible Related Accounts Total Charges $169.34    AccountBalance Balance ($169.34)    Account Number:
                                                            Audited Balance ($169.34)

Adjustment Information

Reason for Adjustment    [Adjust off late Charges ⌄]

Amount of Adjustment    [$6.78]

Service Code    [APRIMEMCO-ADJ ⌄]

[ OK ]   [ Reset ]   [ Cancel ]

Workload Estimate Report
Maryland General
As of 10/21/02

| Designation / Score | Number of Accounts | Minutes to Analyze Each Account | Total Minutes Required | Estimate of Hours Required to Resolve |
|---|---|---|---|---|
| Medicare | | | | |
| 0 | 243 | 10 | 2430 | 41 |
| 1 | 136 | 8 | 1088 | 18 |
| 2 | 50 | 6 | 300 | 5 |
| 3 | 9 | 4 | 36 | 1 |
| 4 | 13 | 2 | 26 | 0 |
| 5 | 28 | 1 | 28 | 0 |
| Patient Payment | | | | |
| 3 | 1 | 2 | 2 | 0 |
| 4 | 11 | 1 | 11 | 0 |
| 5 | 4 | 1 | 4 | 0 |
| Allowance Error | | | | |
| 1 | 2 | 2 | 4 | 0 |
| 2 | 11 | 2 | 22 | 0 |
| 5 | 21 | 1 | 21 | 0 |
| Small Balance | | | | |
| 0 | 4 | 1 | 4 | 0 |
| 1 | 2 | 1 | 2 | 0 |
| All Others | | | | |
| 0 | 113 | 10 | 1130 | 19 |
| 1 | 132 | 8 | 1056 | 18 |
| 2 | 14 | 6 | 84 | 1 |
| 4 | 4 | 2 | 8 | 0 |
| 5 | 5 | 1 | 5 | 0 |
| Grand Total | 803 | | 6261 | 103 |

FIG. 29A

Auditing System

HOME website. contact us. help

Medicare Form 838

MEDICARE CREDIT BALANCE REPORT
(FORM HCFA 838)

Page 1 of 1

PROVIDER NAME: General Hospital
PROVIDER NUMBER: 210038   Contact Person: Stone, Mike
QUARTER ENDING: 12/31/02
MEDICARE PART: A   Phone No. (410)560-6700

| (1) Beneficiary Name | (2) HIC Number | (4) Type of Bill | (5) Admission Date (MM/DD/YY) | (7) Paid Date (MM/DD/YY) | (9) Amount of Credit Balance | (10) Amount Repaid | (11) Method of Payment | (12) Medicare Amount Outstanding | (13) Reason for Credit Balance | (14) Value Code |
|---|---|---|---|---|---|---|---|---|---|---|
| BROWN, MABEL | 217013558D | 111 | 08/11/01 | 11/06/01 | $500.08 | 0.00 | A | $500.08 | 3 | |
| CARPENTER, RUTH | 219167337D | 111 | 08/06/01 | 08/28/01 | $452.22 | 0.00 | A | $452.22 | 3 | |
| HARRY, ELLA | 239601369A | 111 | 07/01/02 | 07/16/02 | $2,214.52 | 0.00 | A | $2,214.5 | 1 | |
| OLIVER, BEN | 250360982 | 111 | 01/06/02 | 01/22/02 | $2,967.81 | 0.00 | A | $2,967.8 | 1 | |
| OLIVER, BEN | 250360982 | 111 | 01/06/02 | 01/22/02 | ($2,967.81) | 0.00 | A | ($2,967.1) | 1 | |

[ Update ] [ Submit ] [ Reset ] [ Cancel ]

FIG. 29B

Auditing System

HOME website . contact us . help

Medicare Form 838

MEDICARE CREDIT BALANCE REPORT
(FORM HCFA 838)

PROVIDER NAME: General Hospital
PROVIDER NUMBER: 210038
QUARTER ENDING: 12/31/02
MEDICARE PART: B Page 1 of 1

Contact Person: Stone, Mike
Phone No. (410)560-6700

| (1) Beneficiary Name | (2) HIC Number | (4) Type of Bill | (5) Admission Date (MM/DD/YY) | (7) Paid Date (MM/DD/YY) | (9) Amount of Credit Balance | (10) Amount Repaid | (11) Method of Payment | (12) Medicare Amount Outstanding | (13) Reason for Credit Balance | (14) Value Code |
|---|---|---|---|---|---|---|---|---|---|---|
| ADAMS, PHYLLIS | NA | 131 | 09/20/01 | 09/10/02 | $82.87 | 0.00 | A | $82.87 | 1 | |
| ADAMS, ROBERT | XMB21750242 | 131 | 03/14/02 | 04/16/02 | $75.84 | 0.00 | A | $75.84 | 1 | |
| ADAMS, ROBERT | XMB21750242 | 131 | 03/14/02 | 04/16/02 | $75.84 | 0.00 | A | $75.84 | 1 | |
| BARZETTI, ADA | XMB20037039 | 131 | 07/02/02 | 09/17/02 | $285.43 | 0.00 | A | $285.43 | 1 | |
| BATES, PATRICK | 212056622C1 | 131 | 08/14/95 | 12/17/96 | $204.65 | 0.00 | A | $204.65 | 1 | |
| BOSTON, ANTHONY | 218901662A | 131 | 07/11/01 | 08/07/01 | $117.35 | 0.00 | A | $117.35 | 2 | |
| BOWYER, MARK | 218302108A | 131 | 11/02/01 | 06/04/02 | $24.00 | 0.00 | A | $24.00 | 2 | 12 |
| BUTLER, EDITH | 220077321D | 131 | 02/09/01 | 01/15/02 | $124.97 | 0.00 | A | $124.97 | 1 | |
| CARTER, DAISY | 230147236D | 131 | 02/16/99 | 03/23/99 | $64.37 | 0.00 | A | $64.37 | 2 | 43 |
| EPPS, GEORGE | 229623030A | 131 | 01/07/02 | 03/26/02 | $58.13 | 0.00 | A | $58.13 | 1 | |
| GREEN, NAOMIA | 577528238A | 131 | 12/28/00 | 01/23/01 | $294.54 | 0.00 | A | $294.54 | 3 | |
| LEE, CYNTHIA | 219161963C1 | 131 | 03/07/02 | 09/24/02 | $49.70 | 0.00 | A | $49.70 | 3 | |

PATIENT CREDIT BALANCE ACCOUNT ANALYSIS, OVERPAYMENT REPORTING AND RECOVERY TOOLS

FIELD OF INVENTION

This invention generally relates to the health care industry. In particular, the invention relates to managing, analyzing and reporting credit balance accounts of overpaid claims.

BACKGROUND

Analyzing credit balance accounts in the health care industry is an arduous and difficult task. A health care facility, such as a hospital, deals with hundreds of patients on a daily basis. For each service that a patient receives, a fee or multiple fees are charged for the service. The service fees are tracked through patient accounts. Each patient account has information concerning the service(s) rendered, the fee amount and any financial transactions made for the service. Payments for the service may be paid by Medicare, a health insurance payer or payers, the patient or a combination of them. Also, since the health care facility may make arrangements with Medicare and certain health care payers for discounts in the service fee, the account tracks these adjustments. As a result, for each date of service for a patient, an account is produced with fees, payments and discounts.

Due to the large number of these transactions occurring, errors or discrepancies may occur. To illustrate, an insurance company and the patient may both pay the entire amount for a service, creating a double payment for a service.

Correcting these errors and discrepancies is a long and arduous process. Typically, a group of adjusters will review each account to find errors and correct them. A manager of the group will divide the accounts among the adjusters and each adjuster will sequentially work through his/her accounts. To analyze an account, the adjuster pulls the patient account up on the health care facility's computer system by navigating through many screens. Each screen displays different information concerning the account. After reviewing the information on the screens, the adjuster may be able to resolve the error or may require additional information, such as an explanation of benefits (EOB). If additional information is required, the adjuster requests the information by filling out a form. After the adjuster receives the information, the adjuster will proceed in resolving the error or discrepancy. This approach takes a considerable amount of time. The adjuster must navigate through sometimes dozens of screens, make manual calculations, and request additional information in order to resolve the account.

Additionally, the manager/adjuster typically has no or little foreknowledge of the accounts prior to beginning the account analysis. As a result, the accounts may not be processed in an efficient manner. Difficult to resolve accounts may be given to inexperienced adjusters, instead of experienced adjusters. Accounts easily resolved dealing with large amounts of money may not be processed until after difficult accounts dealing with small amounts.

Also, reports must be made quarterly to Medicare regarding Medicare overpayments. These reports are derived from the patient credit balance accounts. As a result, errors in the patient credit balance accounts or patient credit balance accounts having Medicare overpayments not discovered leads to errors in the Medicare reports. Any errors in these reports can lead to civil and criminal penalties.

Accordingly, it is desirable to have better tools for managing, analyzing and resolving credit balance accounts.

SUMMARY

The present invention provides a system for managing, analyzing, reporting and resolution of credit balance accounts, although various components and features of the system are inventions into themselves. Certain aspects of the invention allow managers of both service providers (such as health care facilities) and payers (such as insurance companies and Medicare) to assign work and produce reports. Other aspects of the invention allow provider users and payer users to analyze and resolve the claims in an automated environment. These aspects provide the users with information in a readily accessible and easy to navigate format.

BRIEF DESCRIPTION OF THE DRAWINGS

The foregoing summary, as well as the following detailed description of the preferred embodiment of the present invention, will be better understood when read in conjunction with the appended drawings. For the purpose of illustrating the invention, there is shown in the drawings an embodiment which is presently preferred. It is understood, however, that the present invention is not limited to the precise arrangement and instrumentality shown. In the drawings:

FIG. 4 is an illustration of a demographics screen.

FIG. 5 is an illustration of a notes screen.

FIG. 7 is an illustration of a possible related accounts screen.

FIG. 8 is an illustration of an audit history screen.

FIG. 9 is an illustration of an explanation of benefits request form.

FIG. 10 is an illustration of a desired refund worksheet.

FIG. 11 is an illustration of a patient/insurance refund letter.

FIG. 14 is an illustration of a calculator screen.

FIG. 15 is an illustration of an insurance priority pop-up window.

FIG. 16 is an illustration of a payment/adjustment summary pop-up window.

FIG. 17 is an illustration of a calculate percentage pop-up window.

FIG. 19 is an illustration of a post a refund screen.

FIG. 21 is an illustration of a reverse adjustment screen.

FIG. 29A is an illustration of a Medicare Form 838 (Inpatient).

FIG. 29B is an illustration of a Medicare Form 838 (Outpatient).

DETAILED DESCRIPTION OF THE PREFERRED EMBODIMENT

Certain terminology is used in the following description for convenience only and is not limiting. The term "Medicare Refund Compliance Form," as used in the specification and claims, means "the Medicare 838 form or any form later adopted by Medicare for use in reporting refunds due to Medicare." The words "a" and "one", as used in the claims and in the corresponding portions of the application, are defined as including one or more of the referenced item unless specifically stated otherwise. This terminology includes the words above specifically mentioned, derivatives thereof, and words of similar import.

Figure 1:
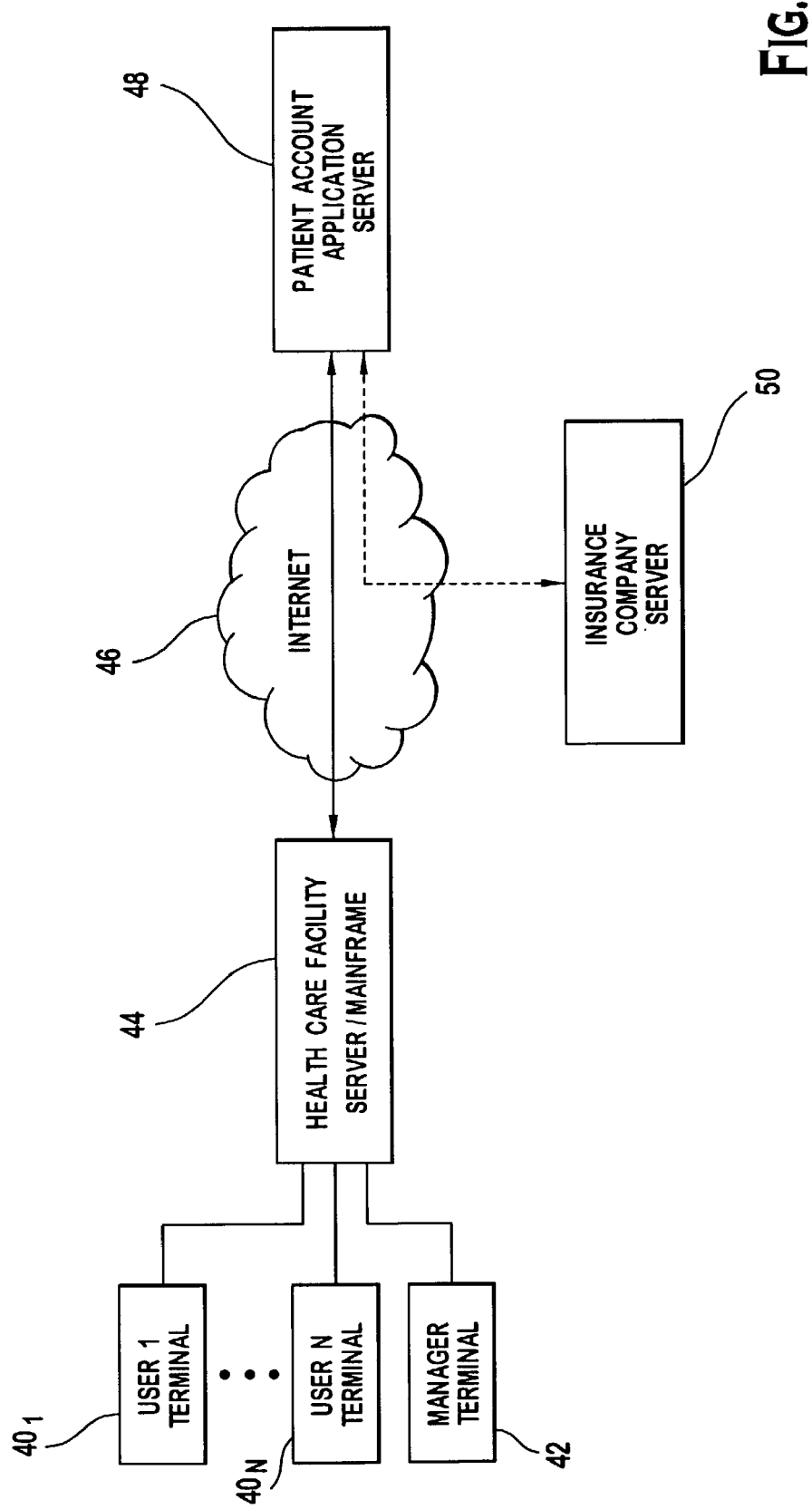
FIG. 1 is a preferred patient account analysis system.

FIG. 1 is a simplified block diagram of a preferred patient account analysis system. Stored on a server or mainframe 44 of a health care facility is the patient account information. The information is typically stored in a database format accessible by users. The typical graphical user interface to access this information uses menu driven screens.

To initiate use of the patient credit account analysis tools, the patient account information is sent to a patient account application server 48, such as by using the Internet 46 as shown in FIG. 1 or by another file transfer technique. Although the device providing the analysis tools is referred to as a preferred patient account application server 48, the device providing the analysis tools may be any processing device. The patient account application server 48 reformats the information into a format more compatible with utilizing the analysis tools. Various analysis tools are utilized to analyze the information of the accounts for eventual use by auditors (users) and managers.

Users desiring to analyze the accounts use the patient credit account tools, such as by using user terminals (user 1 terminal $40_1$ to user N terminal $40_N$). The users use the tools to retrieve and modify information on the patient account application server 48. Although the users and manager are illustratively shown for a preferred application at the health care facility, the users may be at another site (not at the health care facility) or multiple sites, accessing and modifying patient account information through various computer or electronic means.

To analyze an account, the account record is checked out by the user so that only one user can work on an account at a time. The patient account application server 48 will not allow another user to modify a checked out account. After the user is finished with the account, the account must be checked in before another user can view, modify or further process the account.

A manager, such as by using a manager terminal 42, can analyze and assign accounts to users using the analysis tools. Although the manager is illustratively shown as accessing the analysis tools through a manager terminal 42, typically, the manager gains access by being assigned managerial access through the sign in procedure. After the users modify information on the patient account application server 48. The changed information is sent, such as manually in a batch or electronically, from the patient account application server 48 to the health care facility server 44 to replace the corresponding information.

Optionally, as shown in FIG. 1 by the dotted lines, the patient account application server 48 may also be connected to one or multiple insurance company servers/mainframes 50. This connection facilitates updating information at the insurance company server 50 and the transfer of funds between the health care facility and insurance companies.

Although the preferred system is described in the context of the preferred web based system, it is adaptable to other implementations. The analysis tools may be made available through a wide area network (WAN) or a local area network (LAN). The tools may also be made available by installing software at the health care facility or other techniques.

Figure 2:
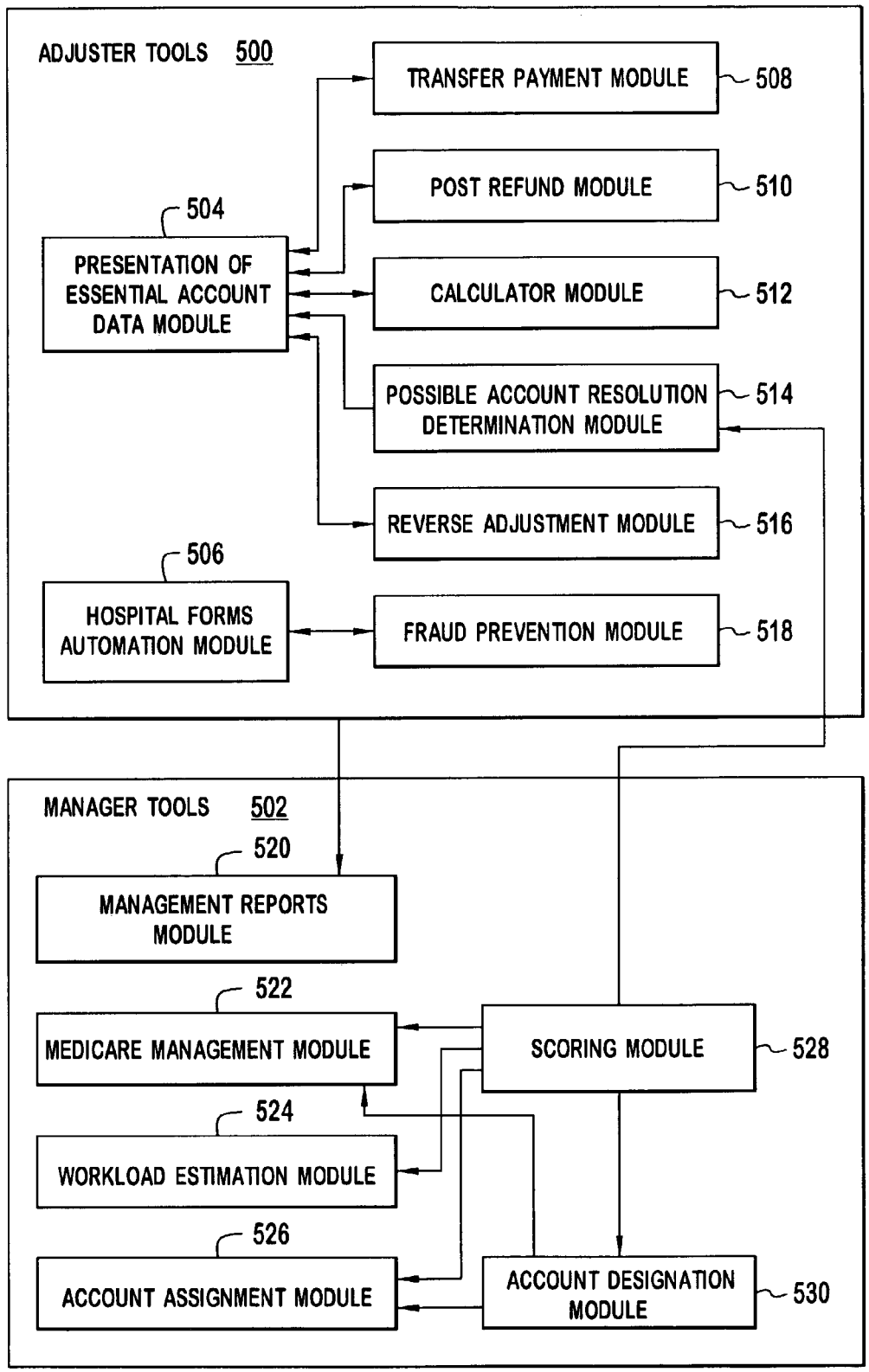
FIG. 2 is an illustration of the adjuster and manager tools.

The software of the system in the preferred implementation allows for an automated account analysis, overpayment reporting recovery tools. The tools can be broadly categorized in two categories as shown in FIG. 2: adjuster tools 500 and manager tools 502.

The adjuster tools 500 allow an adjuster to analyze and resolve accounts almost entirely within the software of the system. These tools allow the auditor to quickly process the accounts with minimum interaction outside the system. To accomplish this, the adjuster tools 500 has a presentation of essential account data module 504, transfer payment module 508, post refund module 510, reverse adjustment module 516, calculator module 512, possible account resolution determination module 514, hospital forms automation module and fraud prevention module 518.

The presentation of essential account data module 504 presents account data to the adjuster in a readily accessible and easy to navigate GUI. The transfer payment module 508 automates the transfer of payments between accounts. The post refund module 516 automates the posting of refunds. The reverse adjustment module 516 automates the posting of reverse adjustments. The calculator module 512 allows the adjuster to make calculations in an automated fashion. The possible account resolution determination module 514 provides the adjuster with an estimate of the problem with the account, allowing the adjuster to more quickly resolve the account. The determination module 514 uses data from the scoring module 528 in the managerial tools 502 to make the problem estimation. The hospital forms automation module 506 allows the adjuster to complete routine hospital forms in an automated manner. The fraud prevention module 506 reduces the possibility of an adjuster committing fraud.

The backbone to the managerial tools 502 is the scoring module 528. The scoring module 528 analyzes the accounts for certain criteria and scores the accounts as to the difficulty in resolving the accounts. The account designation module 530 takes information determined by the scoring module 528 and categorizes each account. An account assignment module 526 allows a manager to assign accounts to adjusters in an efficient manner. The assignment module 526 may use the account designation and score in the assignment at the manager's discretion. The workload estimator 524 estimates the labor required to resolve the accounts based on the account designation and score. The Medicare management module 522 automates and simplifies complying with Medicare's credit balance regulations. The module 522 uses the Medicare account designation information from the account designation module 530 and the score of those accounts from the scoring module 528 in producing Medicare related reports. The management reports module 520 provides managers with audit, management, profit and administrative reports. The management reports module 520 uses information from the adjusters' tools in generation of some of the reports.

These modules provide a highly automated environment for managing, analyzing and reporting accounts of overpaid claims. Although the overall system is described as one system, each module and module feature may be used without the other module features.

The preferred implementation of the patient account analysis tools uses information from the health care facility's server/mainframe 44 and arranges the information in a readily accessible and easy to navigate GUI. In a preferred implementation, the client transfers information from the server/mainframe 44 using a batch process. A batch file is created and such as by using file transfer protocol (FTP), the file is transferred for use by the analysis tools. The preferred GUI presents information using a six screen interface, although other GUIs may be used. The six screens are a payments screen 52 (FIG. 3), a demographics screen 102 (FIG. 4), a notes screen 120 (FIG. 5), an insurance information screen 130 (FIG. 6), a possible related accounts screen 144 (FIG. 7) and an audit history screen 158 (FIG. 8). The preferred GUI is configured to expedite the analysis of the credit balance accounts.

Figure 3:
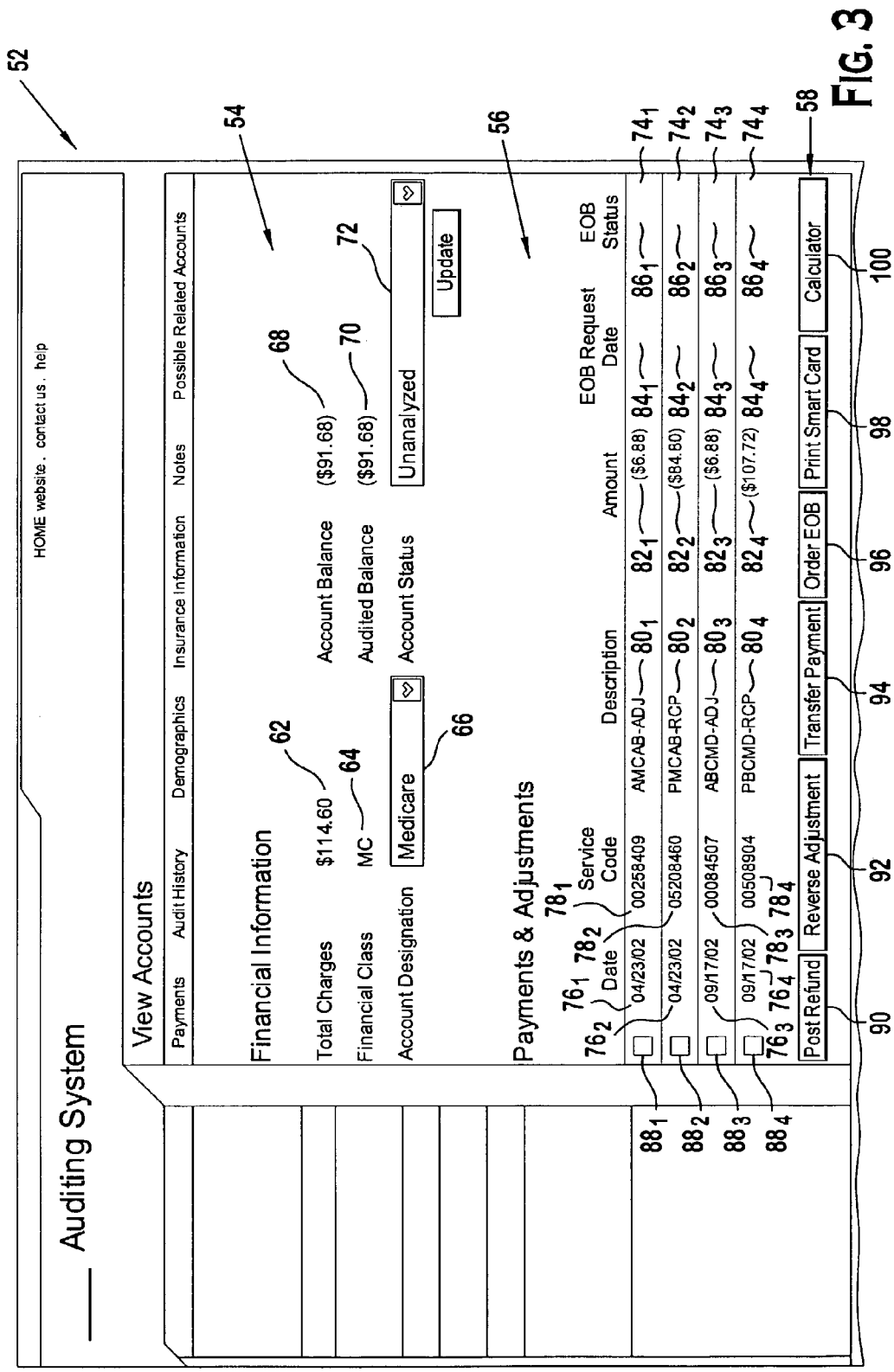
FIG. 3 is an illustration of a payments screen.

FIG. 3 is an illustration of a payments screen 52. The payment screen 52 contains certain patient demographic data (e.g. name and account number) and is divided into three main sections: a financial information section 54, a payments and adjustments section 56 and a function icons section 58.

The financial information section 54 provides a financial summary of an account. As illustrated in FIG. 3, the financial information includes the total charges for the service(s) 62, an account balance 68, a financial class 64, an account designation 66, an audited balance 70 and an account status 72. The total charges field 62 indicates the total charges for the account. The account balance 68 is the resulting balance on the account determined by subtracting all payments and adjustments in the Payments and Adjustments section 56 from the Total Charges field 62. The financial class 64 typically indicates the primary insurance for this date of service as determined by the health care facility. The account designation 66 is an indicator of the type of account. An audited balance 70 is the balance of the account after auditing.

The account status 72 indicates the extent that the account has been previously audited. The account status preferably has six designations: "Unanalyzed", "Audited", "Resolved Outside of System", "Waiting for EOB", "No EOB" and "Need Assistance". The "Unanalyzed" designation indicates that the account has not been audited. The "Audited" designation indicates that the account has already been audited. The "Resolved Outside of System" designation indicates that the account has been resolved but not using this interface. The "Waiting for EOB" designation indicates the auditing of the account has been postponed until the EOB is received. The "No EOB" designation indicates that requested EOB(s) were unobtainable. The "Need Assistance" designation indicates that auditing of the account has been postponed until some sort of assistance has been provided to the user. The account status is preferably selected by using a pull-down menu.

The payments and adjustments section 56 includes each payment and adjustment $74_1$ to $74_4$ (74) made to the account. Each payment/adjustment preferably has six fields. The six fields are "Date" $76_1$ to $76_4$ (76), "Service Code" $78_1$ to $78_4$ (78), "Description" $80_1$ to $80_4$ (80), "Amount" $82_1$ to $82_4$ (82), "EOB Request Date" $84_1$ to $84_4$ (84) and "EOB Status" $86_1$ to $86_4$ (86). The "Date" field 76 indicates the date that the payment/adjustment was posted. The "Service Code" field 78 indicates the service code as assigned by the provider associated with the payment/adjustment, including whether it is a payment or adjustment. The "Description" field 80 is a brief description of the payment/adjustment. The "Amount" field 82 indicates the monetary amount of the payment/adjustment. The "EOB Request Date" field 84 indicates the date that an EOB was requested. If the "EOB Request Date" field 84 is blank, an EOB was not requested. The "EOB Status" field 86 indicates the status of obtaining an EOB. If an EOB was not requested, the "EOB Status" field 86 will be blank.

To the left of each payment/adjustment is a checkbox $88_1$ to $88_4$ (88). By selecting the checkbox 88 of a payment/adjustment, that payment/adjustment is selected so that the user can change details of that payment/adjustment, using function icons 58.

The function icons 58 section of the screen preferably has six executable icons. The six icons are "Post Refund" 90, "Reverse Adjustment" 92, "Order EOB" 96, "Transfer Payment" 94, "Print Smart Card" 98 and "Calculator" 100. To execute the "Post Refund" 90, "Order an EOB" 96 or "Transfer Payment" 94 icons, a checkbox 88 next to a payment must have been previously selected. To execute the "Reverse Adjustment" icon 92, a checkbox 88 next to an adjustment must have been previously selected.

FIG. 4 is an illustration of the demographics screen 102. The demographics screen 102 provides general patient information. As shown in FIG. 3, the preferred demographics screen displays the patient's name ("Patient name") 104, the patient's account number ("Account Number") 106, the patient's social security number ("SSN") 108, the patient's date of birth ("DOB") 110, the patient's marital status ("Marital Status") 112, the patient's admittance date to the health care facility ("Admit Date") 114, the individual responsible for paying on the patient's behalf ("Guarantor Name") 116 and the responsible individual's address ("Guarantor address") 118.

FIG. 5 is an illustration of a notes screen 120. Each note on the screen has certain patient demographic information (e.g. patient name and account number, as well as containing three fields: "Post Date" $124_1$ to $124_8$ (124), "Service Date" $126_1$ to $126_8$ (126) and "Note" field 128. The "Post Date" field indicates the date that the note was posted. The "Service Date" indicates the day the service was provided to the patient. The "Note" field has the text information of the note. If the number of notes for an account exceeds a limit, the notes will be displayed on multiple screens. The end user can select between the multiple notes screens 120.

Figure 6:
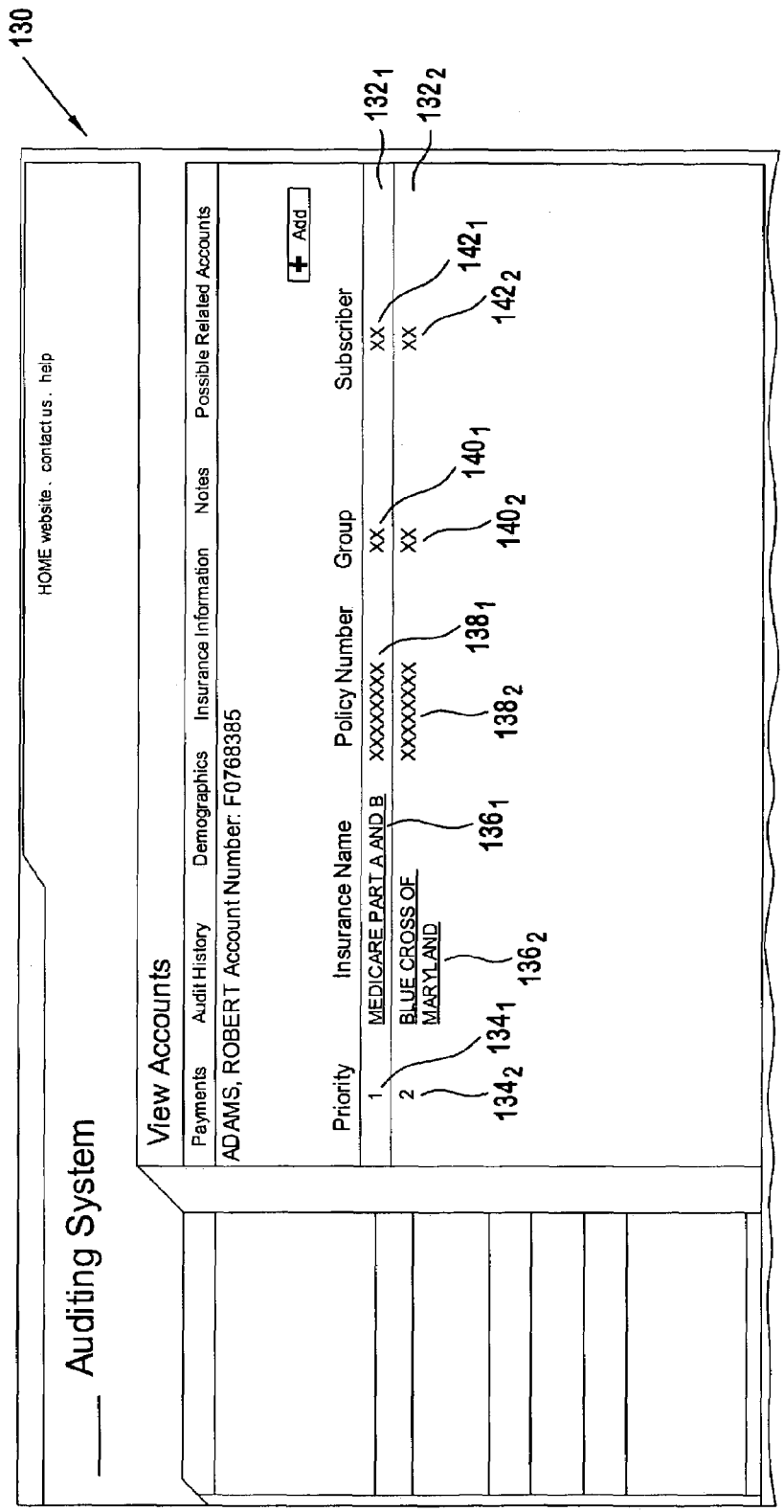
FIG. 6 is an illustration of an insurance information screen.

FIG. 6 is an illustration of the insurance information screen 130. The insurance information screen 130 displays insurance coverage information for the account in addition to certain patient demographic information (e.g. patient name and account number). The insurance coverage information includes Medicare information. Each insurance company $132_1$ to $132_8$ (132) is displayed using five fields: a "Priority" $134_1$ to $134_8$ (134), "Insurance Name" $136_1$ to $136_8$ (136), "Policy Number" $138_1$ to $138_8$ (138), "Group" $140_1$ to $140_8$ (140) and "Subscriber" field $142_1$ to $142_8$ (142). The "Priority" field 134 indicates the order in which the insurance companies pay the patient account. To illustrate, Medicare may have primary responsibility for an account and Blue Cross may be the secondary. The "Insurance Name" field 136 indicates the name of the insurance company. The "Policy Number" field 138 indicates the patient's policy number with the insurance company. The "Group" field 140 indicates the patient's group code with the insurance company. The "Subscriber" field 142 indicates the subscriber.

FIG. 7 is an illustration of the possible related accounts screen 144. The possible related accounts screen 144 aids the adjuster to identify possible payment posting errors. The possible related accounts screen 144 displays information from accounts having the same medical record number. A search of the debit balance account table is conducted for accounts having the same medical record number as the presently displayed account. The information displayed for the matching accounts has six fields: an "Account Number" $146_1$ to $146_8$ (146), "Patient Name" $148_1$ to $148_8$ (148), "Admit Date" $150_1$ to $150_8$ (150), "Discharge Date" $152_1$ to $152_8$ (152), "Total Charges" $154_1$ to $154_8$ (154) and "Balance" $156_1$ to $156_8$ (156) field. The matching accounts are preferably ordered by patient name and then by admit date.

FIG. 8 is an illustration of the audit history screen 158. The audit history screen 158 provides a list of posted audit transactions $160_1$ to $160_3$ (160) made to the account. For each audit transaction 160, six fields are displayed: a "Type" $162_1$ to $162_3$ (162), "Date Posted" $164_1$ to $164_3$ (164), "Amount" $166_1$ to $166_3$ (166), "Service Code" $168_1$ to $168_3$ (168), "Adjustment Reason" $170_1$ to $170_3$ (170) and "Posted By" $172_1$ to $172_3$ (172) field. The "Type" field 162 indicates the general type of the audit transaction, such as being a refund "R" or a transfer "T" of funds. The "Date Posted" field 164 indicates the date that the audit transaction was posted. The "Amount" field 166 indicates the monetary amount of the transaction. The "Service Code" field 168 displays the service code associated with the transaction. The "Adjustment Reason" field 170 provides a short description of the reason for the adjustment, such as "Refund to Medicare Part A and B". The "Posted By" field 172 indicates the user who posted the audit transaction and that user's company.

Beside each refund audit transaction is an editing icon $174_1$ to $174_2$ (174). By a user selecting the editing icon 174, that refund audit transaction can be edited. The audit history screen 158 also has three additional icons: "Print Letter" 176, "Print Form" 178 and "Show Refund" 180. These icons are used with refund transactions. The "Print Letter" icon 176 calls an application for printing a refund letter. The "Print Form" icon 178 calls an application for printing refund authorization forms. The "Show Refund" icon 180 displays details of the refund. The organization and configuration of these preferred screens allows a user to efficiently resolve accounts.

The present invention preferably includes a module that automatically completes standard forms used by hospitals during the process of correcting credit balances in patient accounts. By automating the forms used during the process, significant savings in time is obtained. Such standard forms include, but are not limited to, Explanation of Benefit Requests (hereinafter also referred to as "EOBR"); Check Request Forms; Refund Forms; Letters to Patients/Insurers; and an Account Summary (also referred to as a Smart Card).

Often when analyzing patient accounts it is necessary to collect information regarding the type of services and payments collected for a particular transaction. Prior to this invention, an adjuster would need to complete a separate EOBR that would then be submitted to a separate department to request a copy of EOB. Referring to FIG. 8, The present invention allows the adjuster to complete an EOBR by simply selecting the "Order EOB" 96 function icon.

After an adjuster selects the "Order EOB" 96 icon, the system automatically completes the EOBR and displays the completed form as shown in FIG. 9. The EOBR preferably includes the following completed fields: an adjuster's name field 182; a date of the EOBR field 184; a patient name field 186; an account number field 188; a transaction description field 190; a transaction payment date field 192; a transaction payment amount field 194; and a comments field 196.

By automatically completing the EOBR an adjuster need only add any needed comments directly into the comments field 196. After the EOBR is completed, the adjuster can have the EOBR transmitted electronically or manually to the appropriate person or department as necessary. The EOBR is preferably stored by the system for subsequent printing if desired. When EOBR reports are printed the date of the EOBR field 184 is not updated. Thus, future reviewers will be able to determine when an EOBR was actually completed. Multiple EOBRs can be printed by selecting the desired transactions from a reports screen (described below).

The present invention can also automatically generate check requests or refund forms for an adjuster to increase the efficiency of account processing. The refund form and check request options are listed under the audit reports and the information can be received by date. Each refund transaction is preferably printed on a separate page, but, when being viewed on a monitor, can be viewed in conjunction with other refund transactions.

A check request or refund form can also be printed on the individual account level. If a transaction is a refund, the adjuster can select the refund transaction by selecting the appropriate icon, such as the print letter icon or the print form icon.

Once the request has been made, the necessary information will be selected from the appropriate patient file and the data will be merged into the desired refund worksheet as shown in FIG. 10. The refund worksheet preferably includes the following completed fields: a patient name field 186; an account number field 188; a facility field 196; a date of service field 198; a refund amount field 200; a refund payable to field 202; a payee address field 204; and an adjuster agency field 206. Additionally, the refund worksheet should also have a payment summary section 208; a refund calculation section 210; and a refund explanation section 212.

By automatically completing the refund worksheet, an adjuster can increase the speed with which accounts can be processed and corrected. The refund worksheet preferably contains all of the information necessary to issue a refund. The patients name, account, and the facility where the transactions occurred are listed. The payee and address of the payee for the refund are identified as well as the agency for whom the adjuster works. The payment summary section 208 preferably identifies the most recent payments, the dates on which the payments were posted; and the amounts of the payments.

The refund calculation section 210 preferably identifies the total charges to the account, the total payments, any hospital allowance, and the resulting patient balance. Each account preferably refers to a single patient visit. Thus, if a patient were to visit a hospital on two separate occasions for different reasons, each visit would generate a different account. The hospital allowance is any amount of the expenses for services that the hospital has agreed to forego payment. This typically occurs when a hospital agrees to give an allowance of a certain percentage in exchange for payment of a fixed amount by an insurer.

Whenever an overpayment is shown in the refund calculation section 210 it is preferable that any corrections to the hospital allowance amount be shown and any balance transfers to other outstanding accounts for the same patient be shown. Once any adjustments or transfers have been taken into account, the remaining refund amount is listed in the refund calculation section 210 and the refund amount field 200. The reason for the refund is preferably entered by the adjuster and is preferably the only field that the adjuster has to fill out. Shortcuts can be created to automatically insert one of many common reasons based on a selection made by the adjuster.

Referring to FIG. 11, the system of the present invention can also generate a patient/insurance refund letter. The letter is includes an address area that includes a payable to field 202 and a payee address field 204. The letter explains that a refund is being sent with the letter and states the amount of the refund using a refund amount field 200.

The letter also preferably includes the necessary information for the payee to process the refund. In the case of the insurer letter shown in FIG. 10, the letter includes all of the information required by the insurer to quickly process the refund and to correct its records. Examples of such information are supplied as: a date of service field 198; a patient policy number field 214; a group number field 216; insurer information; and a refund explanation field 212. The bottom of the letter preferably identifies the adjuster 182. This automated letter provides a significant advantage to insurers as the letter provides all the necessary information to process the refund. If desired by an insurer, the system of the present invention can access the insurer's records, adjust the insurer's records to reflect the refunded payment and send the payment directly to the insurer's financial institution.

The system of the present invention can also print an entire account history, referred to as a smart card by some health care providers. The account history is organized for maximum readability and includes a patient demographic section in the header. The search options for generating smart cards includes account balance, score (as described below), account status, patient status, patient last name, admit date, financial class, and user name.

Figure 12:
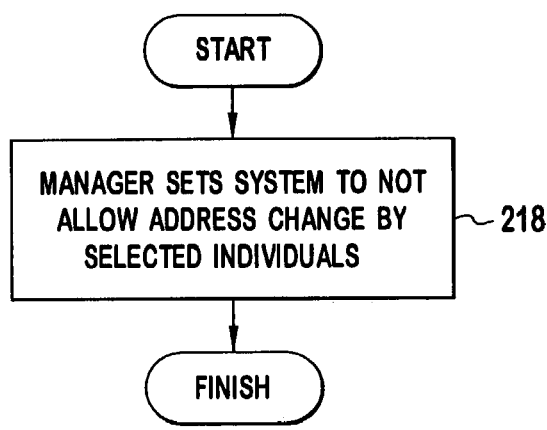
FIG. 12 is a first flow chart of fraud prevention.

The present invention includes a fraud prevention module that is preferably integrated with the hospital forms module. The fraud prevention module preferably has at least two components. The first component as shown in the flow chart of FIG. 12 allows the managers to set the system to not allow designated people, such as adjusters, to change the addresses to which a refund is to be sent, step 218. This helps to eliminate the most common form of fraud in which the address to which the refund is sent is changed by an adjuster.

Figure 13:
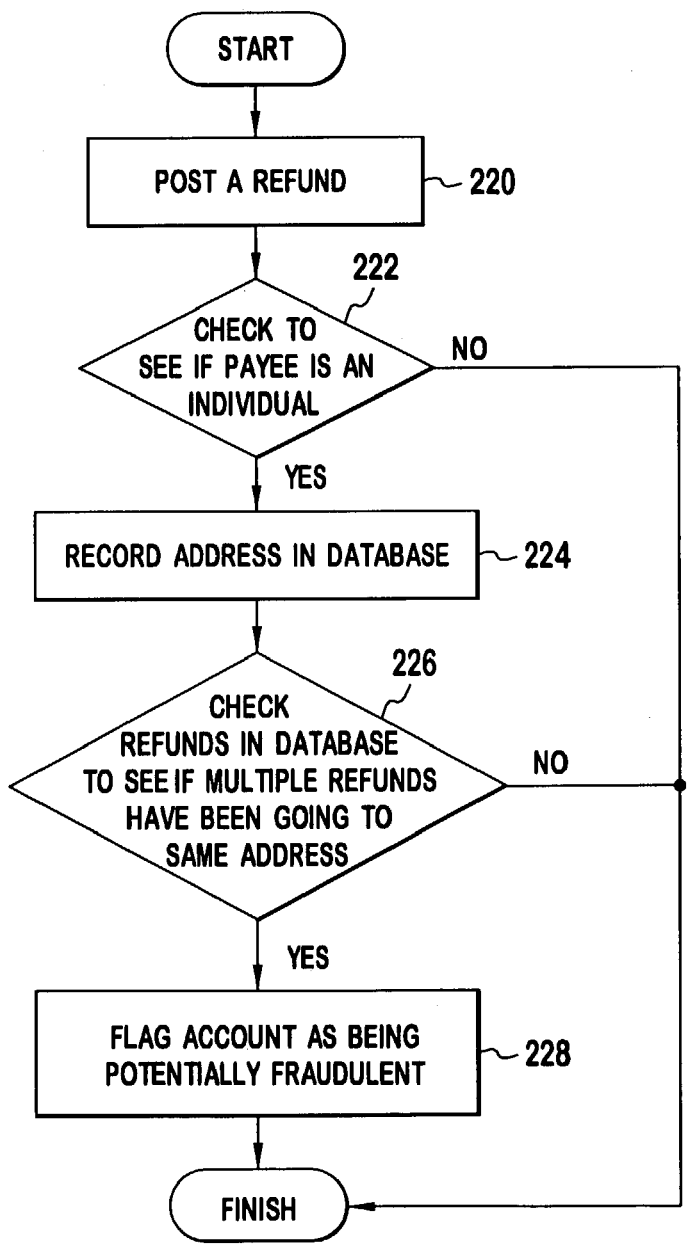
FIG. 13 is a second fraud prevention flow chart.

The second component as shown in the flow chart of FIG. 13 of the fraud prevention module uses a database to track the addresses of each of the refunds sent by the system. Once a refund is posted, step 220, the system checks to see if the payee is an individual and, if so, records the address in a database, step 224. Then, the system checks the database to determine if other refunds have been sent to the same address. If multiple refunds have been sent to a single address, step 226, then the system flags the account to be brought to the attention of a manager, step 228. The flagged accounts are preferably collected in a fraud exception report that can be electronically transmitted to a manager. The fraud exception report can then be used by the manager to review refunds that are potentially fraudulent.

Figure 14:
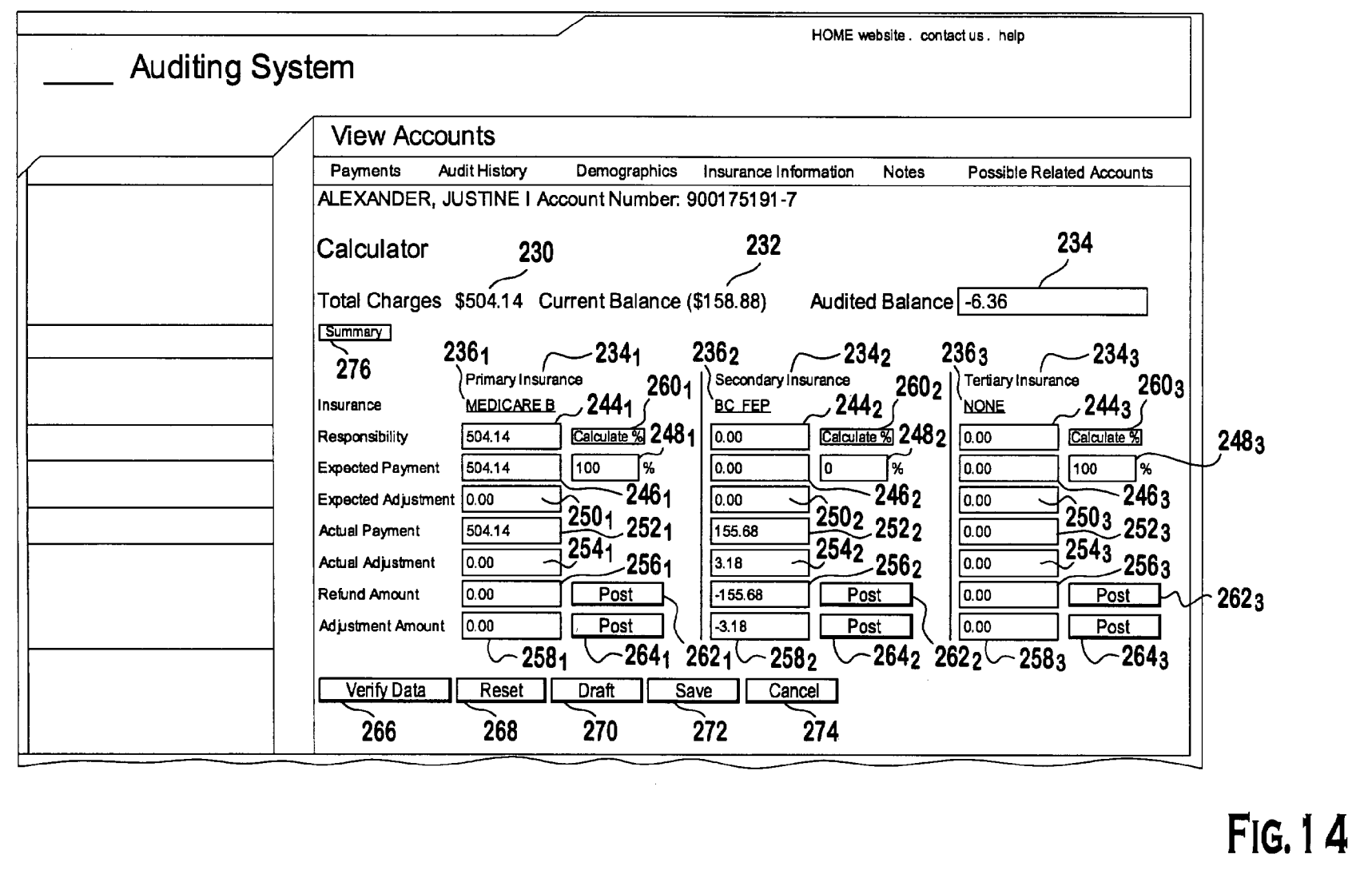

When the calculator icon is executed, a calculator module is retrieved. FIG. 14 illustrates a preferred initial screen for the calculator module. The calculator lists the total charges 230 associated with the account, the current balance for the account and the audited balance 234 at the top of the screen. The audited balance is determined by summing the refund and adjustment amounts and subtracting that value from the current balance 232.

The screen preferably illustrates the insurance information from three insurance providers: a primary $234_1$, secondary $234_2$ and tertiary provider $234_3$. If less than three insurance companies are associated with a file, information for the not used providers is left blank, as illustrated for the tertiary provider. The name $236_1$ to $236_3$ (236) of each insurance provider is listed under each provider. To allow the user to change the insurance companies or the order of the insurance companies, each insurance company name 236 can be executed. When a name 236 is executed, preferably the pop-up window of FIG. 15 is displayed.

Figure 15:
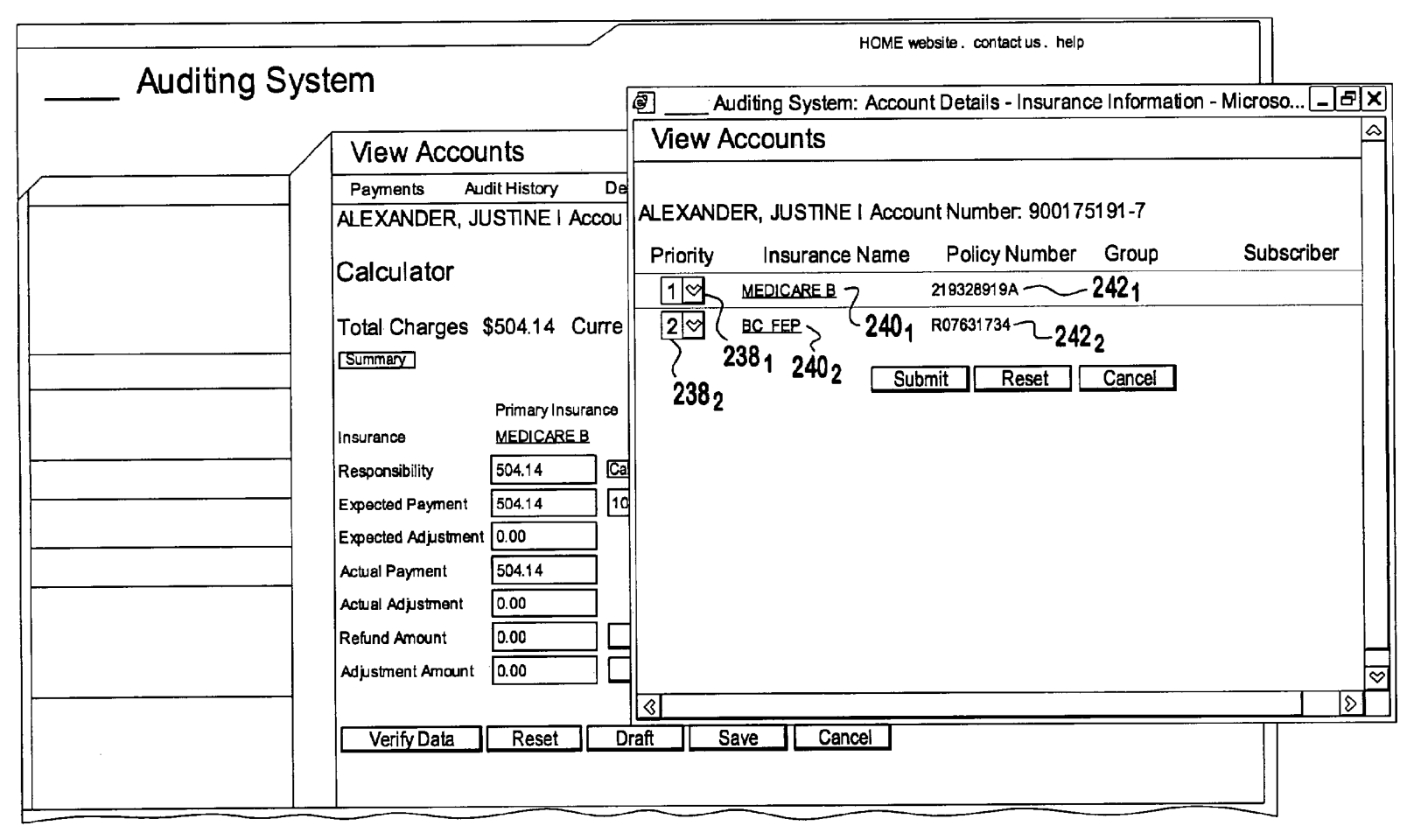

As shown in FIG. 15, next to each insurance company name associated with the account is the priority number $238_1$, $238_2$ for the insurance company. A priority number of 1 indicates the primary insurance company. A priority number of 2 indicates the secondary insurance company and a priority number of 3 indicates the tertiary insurance company. The priority number for each insurance company is preferably selectable using a pull-down menu. Preferably, other information is provided for the insurance companies, such as its name $240_1$, $240_2$; policy number $242_1$, $242_2$; group code and subscriber code.

After the pop-up window is closed, the order of the insurance companies displayed in the screen is per the user selected priority and the insurance table is updated. The updated insurance table contains the previous priority code, the new priority code and the date of the priority change for each modified insurance company. Preferably, the changed priority information is made available for audit reports. If there is an error in the priority number selection, such as two insurance companies having the same priority, an error message is generated prompting the end user to correct the error.

Preferably, eight (8) primary fields are associated with each insurance company displayed in FIG. 14. The eight fields are "Responsibility" $244_1$ to $244_3$ (244), "Expected Payment" $246_1$ to $246_3$ (246), "Percentage" $248_1$ to $248_3$ (248), "Expected Adjustment" $250_1$ to $250_3$ (250), "Actual Payment" $252_1$ to $252_3$ (252), "Actual Adjustment" $254_1$ to $254_3$ (254), "Refund Amount" $256_1$ to $256_3$ (256) and "Adjustment Amount" $258_1$ to $258_3$ (258). Besides the "Expected Payment" field 246 is the "Percentage" field 248.

Each field for each insurance company is input by the user or determined per Table 1. Table 1 also indicates the initial values for the Primary Insurance company. The secondary and tertiary insurance companies are preferably initially set to zero.

TABLE 1

| PRIMARY INSURANCE COMPANY FIELD | VALUE |
| --- | --- |
| Responsibility 244 | Equal to the total charges |
| Expected Payment 246 | Same value as "Responsibility" field |
| Percentage 248 | Expected Payment/Responsibility (Initially 100%) |
| Expected Adjustment 250 | Initially 0 |
| Actual Payment 252 | Total charges + Absolute value of Current Balance |
| Actual Adjustment 254 | Initially 0 |
| Refund Amount 256 | Expected Payment − Actual Payment (Initially Current Balance) |
| Adjustment Amount 258 | Expected Adjustment − Actual Adjustment (Initially 0) |

All of the insurance fields, excluding the "Refund Amount" 256 and "Adjustment Amount" 258, are editable. The "Refund Amount" 256 and "Adjustment Amount" 258 are calculated by the calculator module. During the adjusting, the user may wish to restart the calculations. To restart, the user executes a "Reset" button 268 and the initial values are inserted into the calculator fields. To save a uncompleted calculation, a "Draft" button 270 is executed. To exit the calculator without saving the data, a "Cancel" button 274 is executed.

To aid the user, the "Expected Payment" 246, "Expected Adjustment" 250, "Actual Payment" 252 and "Actual Adjustment" 254 fields can be calculated using a Payment/Adjustment Summary module. The Payment/Adjustment Summary module is preferably retrieved by placing the cursor in one of the fields and executing the "Summary" button 276.

FIG. 16 is an illustration of a Payment/Adjustment Summary pop-up window of the Payment/Adjustment Summary module. The Payment/Adjustment Summary window queries the selected account payments and adjustments for the selected field ("Expected Payment" 246, "Expected Adjustment" 250, "Actual Payment" 252 or "Actual Adjustment" 258 field). The payments 278 and adjustments 280 are grouped by service code $282_1$ to $282_6$ (282) and transaction description $284_1$ to $284_6$ (284). Each group is displayed using the service code 282, transaction description 284 and the sum of the transaction amounts $286_1$ to $286_6$ (286) in the group. Beside each displayed group is a checkbox $288_1$ to $288_6$ (288). The user selects the groups by checking the corresponding checkboxes 288. After the user executes an "OK" button 90, the groups are summed together, the pop-up window is closed and the summed amount is inserted into the selected field. Although not displayed on the calculator screen, the service codes of adjustments used in the summation are stored in a hidden field. The adjustment service codes are carried along for use in subsequently posting an adjustment.

The calculate percentage is changed by executing a "Calculate %" button $260_1$ to $260_3$ (260). Executing the "Calculate %" button 260 displays a calculate percentage pop-up window as shown in FIG. 17. As shown, on the left side of the pop-up window is a list of payments 292 associated with this account. On the right side is a list of adjustments 294 associated with this account. Each payment 292 and adjustment 294 has a transaction description 296 and an amount 298 for the payment or adjustment. Next to each payment 292 and adjustment 294 is a radio button 300. The user selects one payment and one adjustment for the percentage calculation using the radio buttons 300. After selecting the payment and adjustment, the user executes the "OK" button 302. The calculator totals the payment and adjustment together and divides the payment by this total to calculate the percentage. The calculated percentage is inserted into the "Percentage" field 248 and the pop-up window is closed.

To verify data in the fields, the user executes a "Verify Data" button 266. When "Verify Data" button 266 is executed, the data in all fields is checked. The verification process is also evoked, when the user attempts to post a refund or adjustment, by executing a "Post" button $262_1$ to $262_3$ (262), $264_1$ to $264_3$ (264) next to the "Refund Amount" field 256 or the "Adjustment Amount" field 258. When the "Post" button 262, 264 is executed, only data used to determine the refund or adjustment amount is checked.

To verify the data, two checks are performed. In the first check, the values in all the insurance company's "Responsibility" fields 244 are summed to verify that the total equals the "Total Charges" 230 for the account. In the second check, the sum of the "Expected Payment" 246 and the "Expected Adjustment" 250 is checked to verify that the sum equals the "Responsibility Amount". If any of the checks fail, an error message is generated, requiring the user to correct the errors.

To post a refund, the "Post" button 262 next to the "Refund Amount" field 256 is executed. Similarly, to post an adjustment, the "Post" button 264 next to the "Adjustment Amount" 258 is executed. Prior to posting either a refund or adjustment, a verification of that information is evoked. After initiating a post of a refund, a Post Refund module is called. After initiating a post of an adjustment, a Reverse Adjustment module is called.

As shown in FIG. 14, the calculator module has a "Save" button 272. The "Save" button 272 saves the calculated data to the database. Prior to saving the data, the data is verified and if the verification is successful, the data is saved. After the data is saved, the data for that account displayed in the calculator can not be edited and, accordingly, the editing features are removed. After the data has been saved, it can be printed to create a hard copy of the calculations.

After saving the data, if a refund or adjustment were not posted, these buttons 262, 264 are still executable by the user. After the buttons 262, 264 are executed, the buttons are no longer available to the user to avoid a double posting of the refund/adjustment.

Preferably stored with each refund, adjustment and transfer amount is the calculated saved data. By storing this information, a manager is capable of correcting any errors of the users by revising the calculations for the account. The calculator provides a fast and convenient tool for a user to make calculations to resolve an account.

The system of the present invention allows for adjusters to correct patient account credit balances using simple and efficient click through screens. As detailed previously, the standard hospital forms can be automatically completed by selecting the appropriate icons or the like. The use of click through screens allows for quicker account resolution and by automatically processing information contained in the forms, the system reduces the chances of errors due to an adjuster miscopying refund information. The system also verifies the accuracy of transactions that are being posted to an account and records the posting of transactions to be used for audit purposes.

Figure 18:
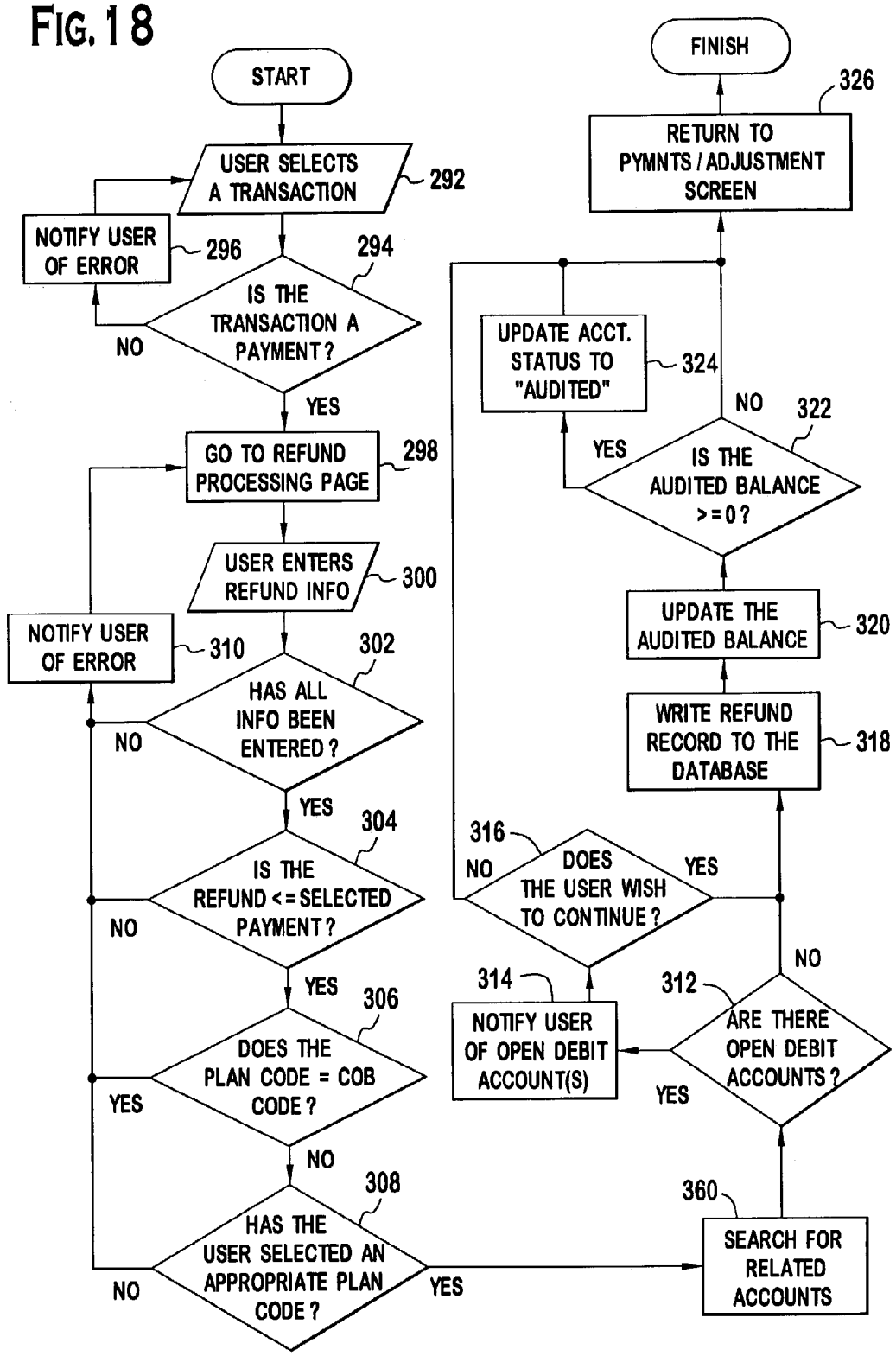
FIG. 18 is a preferred flow chart for posting a refund.

The post refund module is used to post a refund. FIG. 18 is a preferred flow chart for posting a refund. A user selects a payment to post a refund, step 292. The transaction is verified to assure it is a payment, step 294. If not, an error message is generated, step 296. Subsequently, a processing screen is called, step 298. A preferred screen as shown in FIG. 19 has ten fields: "From DOS", "To DOS", "Claim Charges", "Insurance", "Refund Amount", "COB Insurance" (coordination of benefits insurance), "ICN Number" (internal claim control number), "Note Reference", "Explanation" and "Validation Source". These fields are populated by the user, step 300. The "Insurance" and "COB Insurance" fields are preferably populated by the user by selecting an insurance company using a pull-down menu. The insurance companies in the menu are the companies associated with the account that the refund is being posted.

The note reference field is also preferably populated using a pull-down menu. The menu will be populated with notes from the notes reference database table, unless a COB insurance is selected for the "COB Insurance Field". If a COB insurance company is selected, the note reference field is populated with only notes that refer to that COB insurance company.

A list box is preferably located under the explanation text area. The explanation text area is automatically populated with the text of a note reference when one is selected. Additionally, the user can add or edit text in the explanation text area. The "Validation Source" field is preferably populated with checkboxes. Checkboxes can be selected for "System Data", "Called Insurer/Insurers System and "Called Patient".

The "Refund Amount" ("AMT") field is populated by a pop-up screen prior to "Posting a Refund" print screen and is updated by the user in a subsequent screen. The remaining field, "ICN Number", can accept an input from the user. To submit the refund, an "OK" button is executed. A "Cancel" button is also available to cancel the refund at any time. After the "OK" button is executed, the information input into the fields is validated. For a refund to be submitted, the "Insurance", "Refund Amount", "Note Reference", "Explanation" and "Validation" fields need to be completed, step 304. If any of them are not completed an error message is produced and the refund is not posted, step 310.

If a COB note reference is in the "Note Reference" field, the form is checked to verify that the COB Insurance company associated with the note is selected in the "COB Insurance" field, step 306. The refund amount is checked to verify that it is less than or equal to the inverse of the payment amount, step 304, and the insurance company in the "Insurance" field is checked to verify that it is not the same company as the "COB Insurance". The "Validation Source" field is checked to verify that at least one box is checked.

The refund amount is checked against the debit database table, steps 312, 314. If there is a debit amount matching the refund amount, the user is given an opportunity to cancel the transaction, step 316. A final validation is performed for the plan code. The plan code table is checked to see if the plan code associated with the selected insurance company is in the table, step 308. If any of the validations fail, the posting is halted and an error message is generated, step 310. If the refund is validated, it is posted, steps 318, 320. If the audited balance is greater to or equal to zero, step 322, the account status for the account is changed to "Audited", step 324. Preferably, after posting the refund, the user is returned to the payments/adjustments screen, step 326.

If the refund module is called from the calculator module, the refund module will be configured to allow multiple refunds. Each refund is to a different insurance company.

Figure 20:
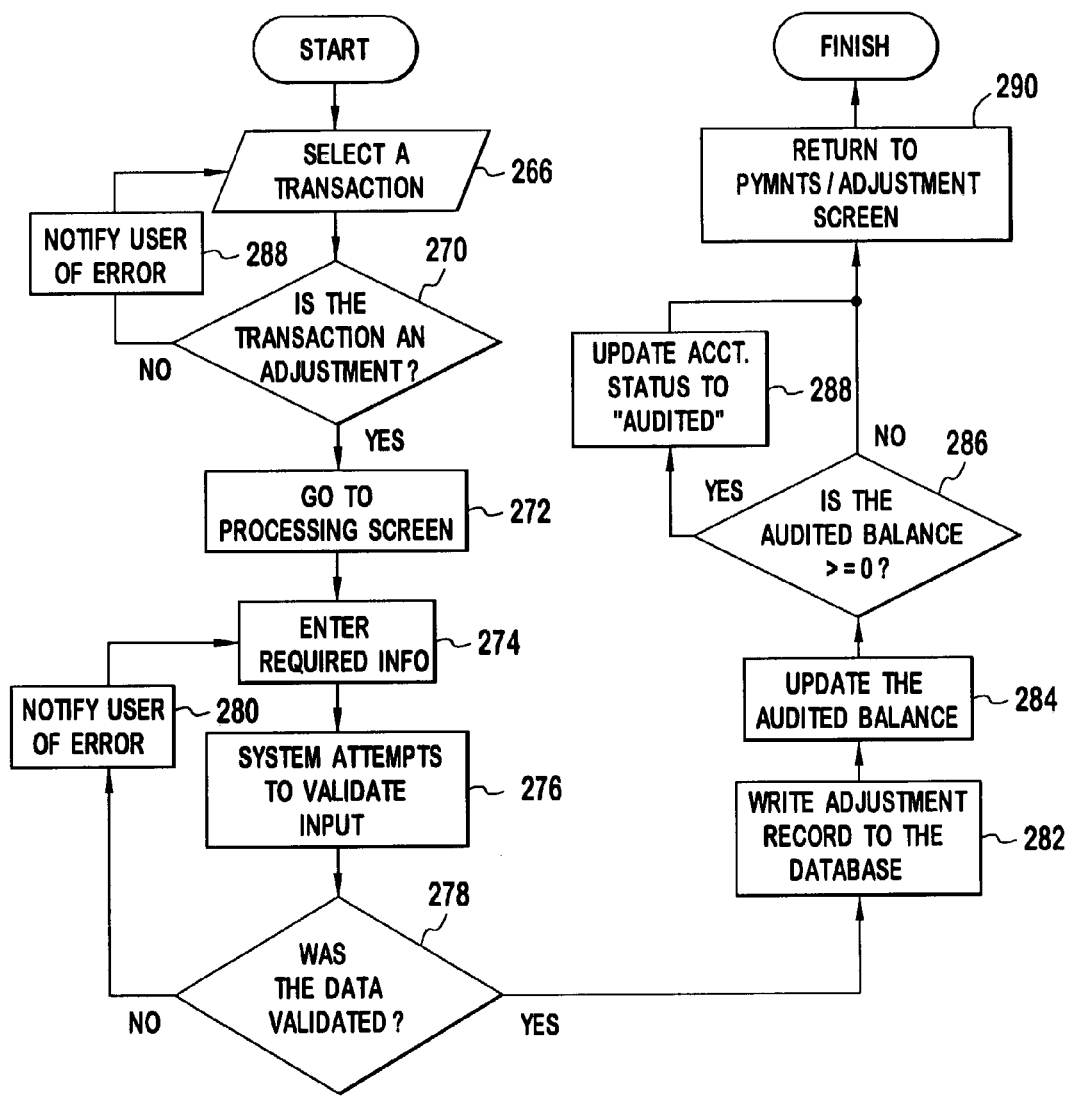
FIG. 20 is a preferred flow chart for reversing an adjustment.

The reverse adjustment module is used to post a reverse adjustment. FIG. 20 is a preferred flow chart for reverse adjusting. A user selects an adjustment to post, step 266. The transaction is verified to assure it is an adjustment, step 270. If not, an error message is generated, step 268. Subsequently, a processing screen is called, step 272. The user enters information into the screen as illustrated in FIG. 21, step 274. The screen has the three fields: "Reason for Adjustment", "Amount of Adjustment" and "Service Code".

The "Reason for Adjustment" field is preferably populated using a pull-down menu. The pull-down menu is populated with items from an adjustment explanation table. The adjustment amount is automatically populated by the module using an inverse value of the selected record. The "Service Code" is a pull-down menu having the provider's insurance codes. The initial value for the service code is preferably the service code of the selected record.

The user posts the adjustment by executing the "OK" button. The adjustment can be cancelled at any time by executing the "Cancel" button. After executing the "OK" button, the adjustment is verified to that the adjustment amount is less than or equal to the amount of the selected record, steps 276, 278. If the adjustment passes the verification, it is posted, steps 282, 284. Otherwise, an error message is generated, step 280. If the audited balance is greater than zero, step 286, the account status is changed to "Audited", step 288. Preferably, after posting, the user is returned to the payments/adjustments screen, step 290.

If the reverse adjustment module is called from the calculator, the calculated adjustment amount is entered into the adjustment amount. The list of service codes in the pull-down window includes the service codes used in the Payment/Adjustment Summary module. If there is a balance for the calculated adjustment after the form is submitted, an adjustment screen is called to resolve the balance.

Figure 22:
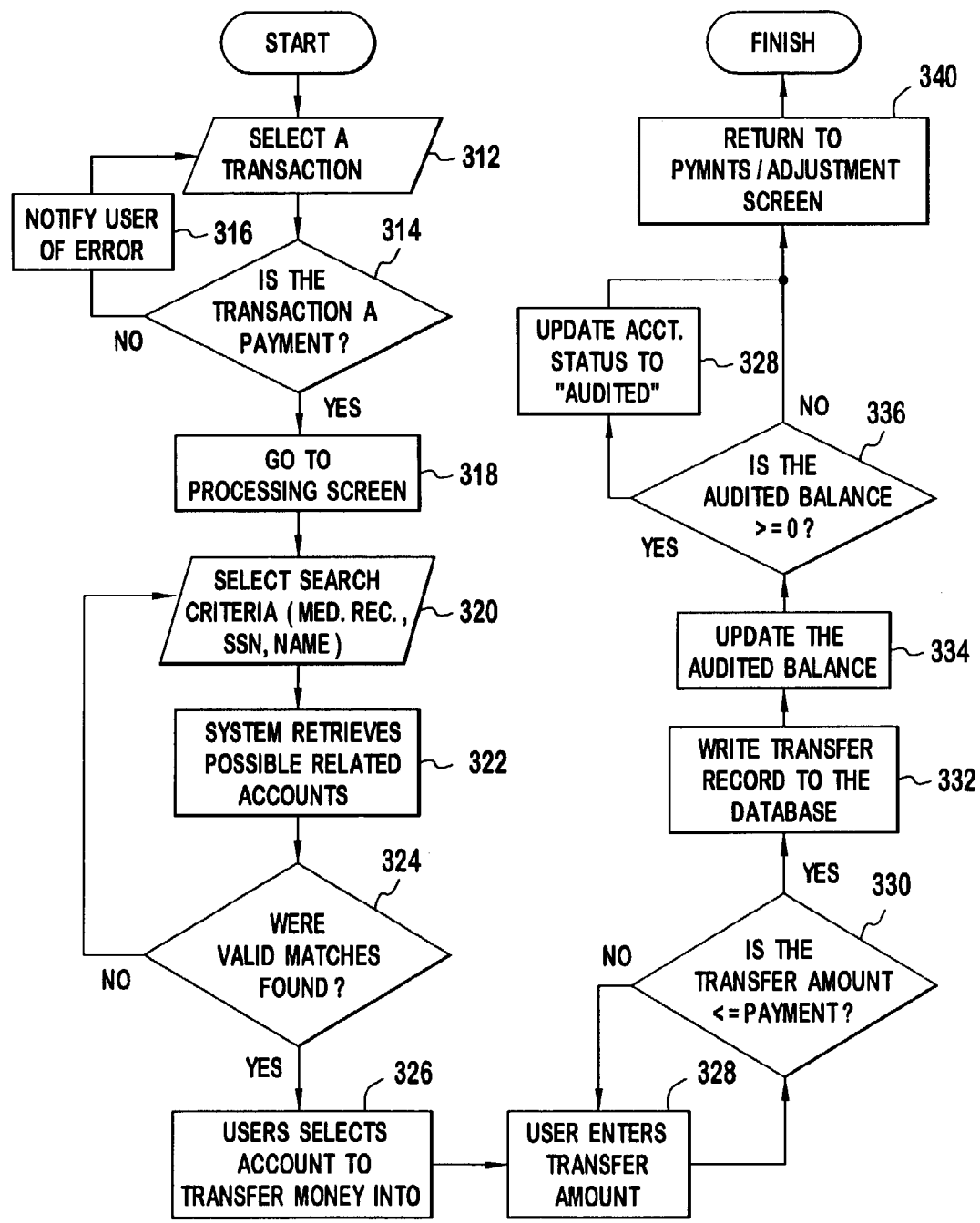
FIG. 22 is a preferred flow chart for transferring a payment.
Figure 23:
FIG. 23 is an illustration of a transfer payment screen.

The transfer payment module is used to transfer payments between accounts. FIG. 22 is a preferred flow chart for transferring payments. A user selects a payment to transfer, step 312. The transaction is verified to assure it is a payment, step 314. If not, an error message is generated, step 316. Subsequently, a processing screen is called, step 318. The transfer payment screen as shown in FIG. 23 has the four primary fields: "Payment Amount", "Transferred to Account", "Search Options" and a "Search Criteria" fields.

The "Payment Amount" field is populated with the value from the selected payment, step 328. The "Transferred to Account" field is a pull-down menu having a listing of accounts associated with the patient, step 326. A radio button by each account allows the account to be selected for the fund transfer. The user can also search for other accounts to transfer funds to using the two Search fields. The "Search Options" field is a pull-down menu containing various search options, such as "Medical Record Number", "Social Security Number" and "Patient Name", step 320. Criteria for the search option is input into the "Search Criteria" Field, step 322. The search results are returned to the user, step 324.

To transfer the payment, the "OK" button is executed. The transfer can be cancelled at any time by executing the "Cancel" button. After the "OK" button is executed, the transfer amount is validated to assure that it is less than or equal to the payment amount and that an account has been selected, step 330. If the validation is failed, an error message is generated. If the validation is passed, the transfer is made, steps 332, 334, and the user is returned to the Payments screen. If the audited balance is greater than zero, step 336, the account status is changed to "Audited", step 328. Preferably, the user is returned to the payments/adjustments screen, step 340.

One analysis tool is referred to as scoring. The scoring tool preferably produces a numeric value indicating the amount of work and the skill level of that work required to resolve a patient credit balance account. This tool aids a manager in assigning the accounts to adjusters.

Figure 24A:
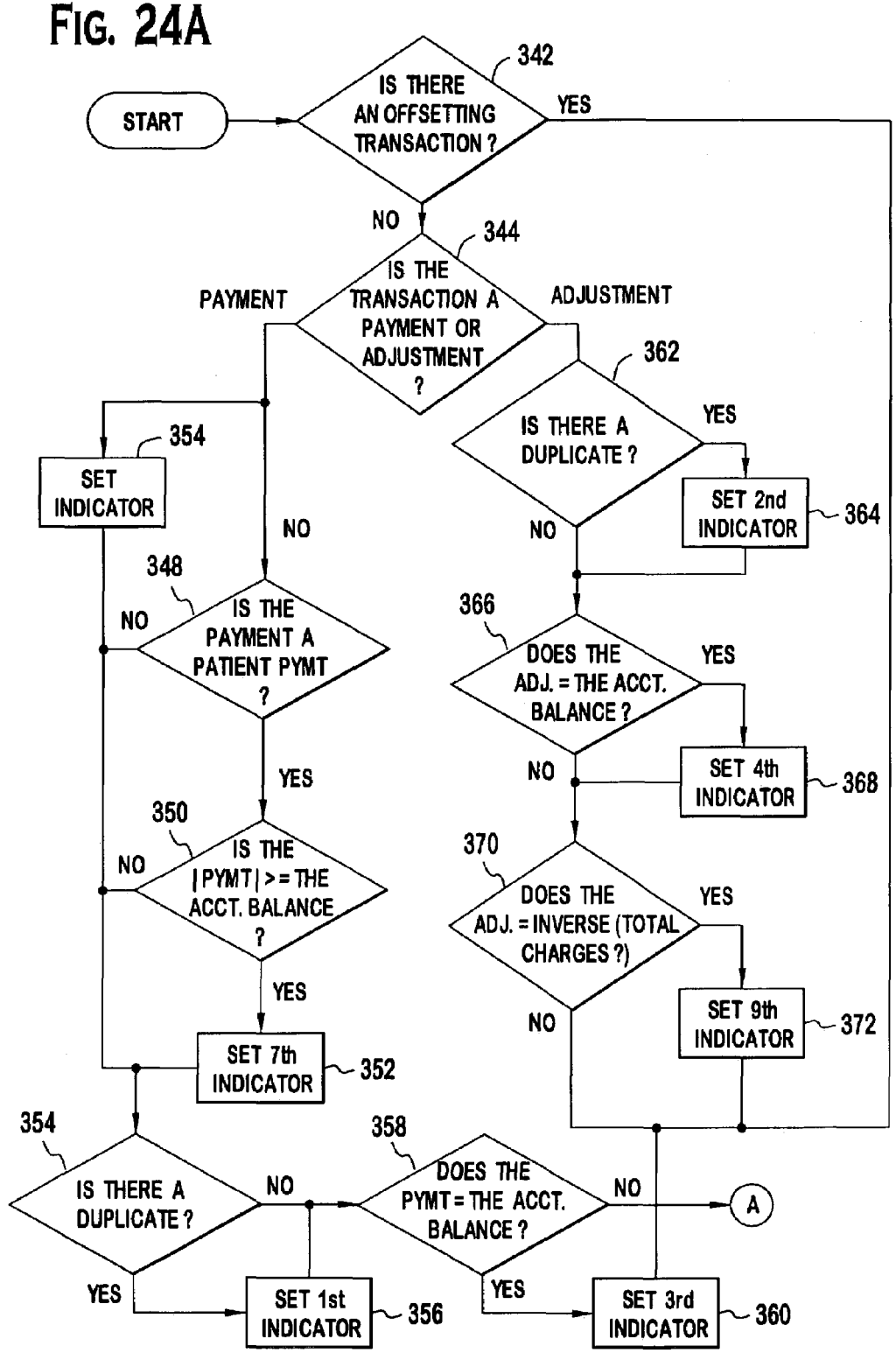
FIGS. 24A and 24B is a preferred flow chart for scoring.
Figure 24B:
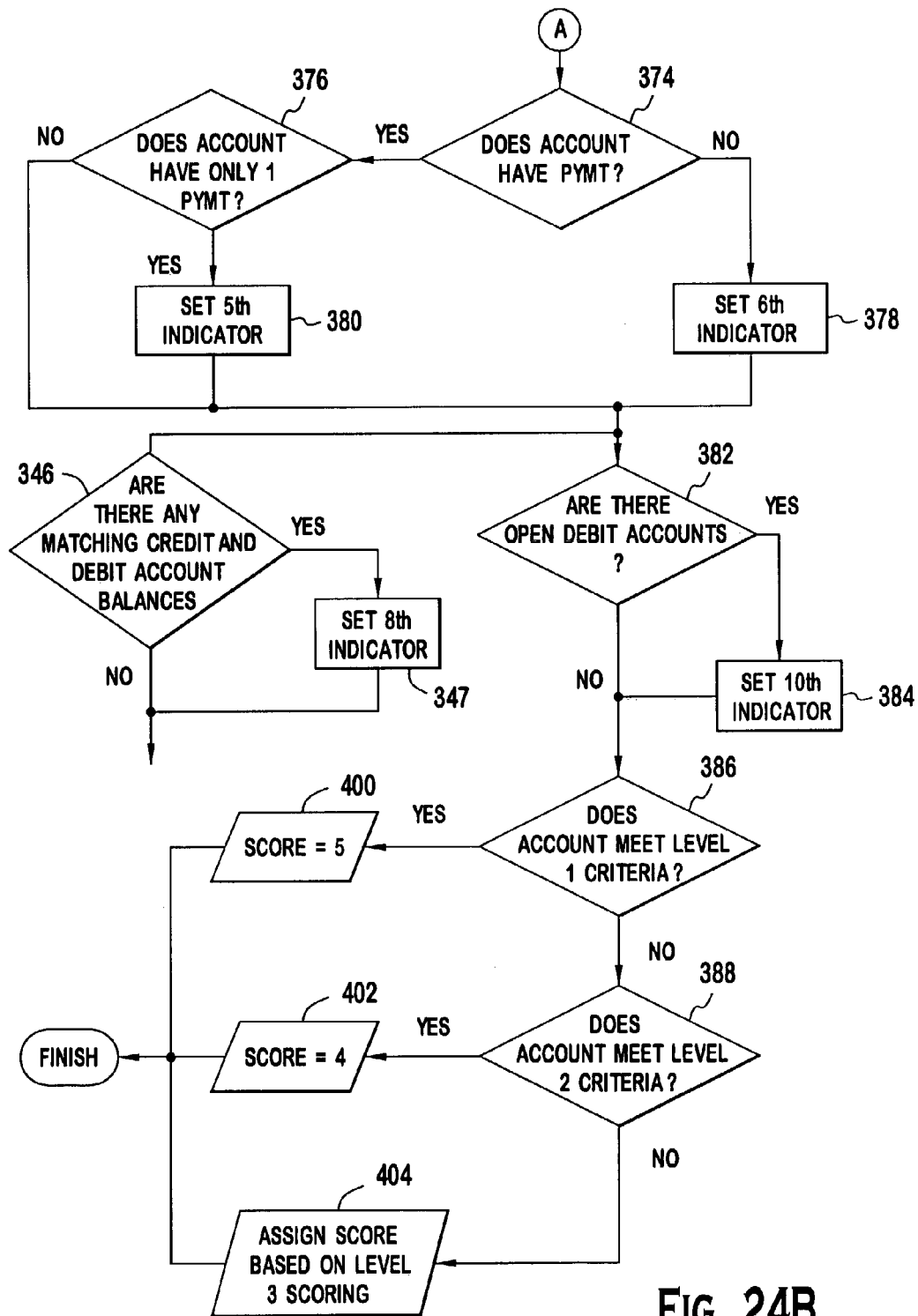

FIGS. 24A and 24B are flow charts of a preferred scoring method, although other variants may be used. The preferred scoring tool assigns each account a numeric value from zero (0) to five (5). A zero (0) indicates a large amount of work at a high skill level is likely required to resolve the account. At the other extreme, a five (5) indicates that a small amount of work at a relatively low skill level is required to resolve the account.

Initially, each account is scored. Since account information may be updated and changed and new accounts may be added, the scoring information may need to be updated. The updating may be performed on a periodic basis or only when requested, such as by a manager. Updated accounts are rescored and new accounts are scored to provide up to date scoring information.

Referring to FIG. 24A, initially, the account is checked for offsetting transactions, step 342. Offsetting transactions are transactions having the same service code, which net to zero. Any offsetting transactions are marked as offsetting and are ignored for the remainder of the scoring process. To score each patient account, the service code on each transaction is checked to see of the transaction is a payment or an adjustment, step 344. After the transaction is deemed a payment or an adjustment, the transaction is marked accordingly.

To score an account, the account is analyzed for certain indicators. The preferred scoring approach uses ten (10) indicators. Once an indicator is found, the transaction and the account tables are updated to mark the account and corresponding transaction with the indicator.

The first indicator (Indicator 1) is whether the account has any duplicate payments, step 354. The account number, transaction type, service code and amount are compared for each payment in the account. If a duplicate payment is found, the account and transactions are marked for the first indicator, step 356.

The second indicator (Indicator 2) is duplicate adjustments, step 362. This search is similar to the search for duplicate payments. The account number, transaction type, service code and amount are compared for each adjustment made to the account. If any of the adjustments match, the account and transactions are marked for the second indicator, step 364.

The third indicator (Indicator 3) is payments that are equal to the account balance, step 360. Each payment in the account is compared to the account balance. If any payment matches the account balance, the account and transactions are marked for the third indicator, step 352.

The fourth indicator (Indicator 4) is adjustments that are equal to the account balance, step 366. Each adjustment in the account is compared to the account balance. If any adjustment matches the account balance, the account and transactions are marked for the fourth indicator, step 368.

The fifth indicator (Indicator 5) is accounts that have only a single payment, step 376. If the account only has a single payment, the account is marked for the fifth indicator, step 380. The sixth indicator (Indicator 6) is accounts having no payments, step 374. If the account has no payments, the account is marked for the sixth indicator, step 378.

The seventh indicator (Indicator 7) is patient payments that are greater than or equal to the account balance, steps 348, 350. The patient payments are identified by their service code and are compared to the account balance. If the patient payments are greater than or equal to the account balance, the account and transactions are marked for the seventh indicator, step 352.

The eighth indicator (Indicator 8) is matching credit and debit account balances, step 346. The medical record number of the account being analyzed is used to find a debit account balance matching this account's credit balance. If a match occurs, both the credit and debit balance accounts are marked with the eighth indicator, step 347.

The ninth indicator (Indicator 9) is adjustments that equal the inverse of the total charges, step 370. If an adjustment in the account equals the inverse of the total charges, the adjustment transaction and the account are marked for the ninth indicator, step 372.

The tenth indicator (indicator 10) is open debit balance accounts for the same patient, step 382. A search is conducted for any open debit account balances for the same patient as the present account. If such an open debit account balance is found, the account is marked for the tenth indicator, step 384.

The indicators are summarized in Table 2.

TABLE 2

| INDICATOR NUMBER | INDICATOR DESCRIPTION |
|---|---|
| 1 | Duplicate payments |
| 2 | Duplicate adjustments |
| 3 | Payment equals account balance |
| 4 | Adjustment equals account balance |
| 5 | Only a single payment in the account |
| 6 | No payments in the account |
| 7 | Patient payment is greater than or equal to the account balance |
| 8 | Matching credit and debit account balances |
| 9 | Adjustment equals the inverse of the total charges |
| 10 | Open debit account balances for the same patient |

After the indicators have been identified, the accounts are scored. Table 3 lists level 1 criteria. Any account meeting the level 1 criteria is provided a score of 5 as being quickly resolved by an adjuster having a lower skill level, steps 386, 400.

TABLE 3

| LEVEL 1 CRITERIA |
|---|
| INDICATOR 8 AND INDICATOR 7 |
| INDICATOR 8 AND INDICATOR 5 |
| (INDICATOR 3 OR INDICATOR 4) AND INDICATOR 9 |
| INDICATOR 2 AND THE DUPLICATE ADJUSTMENT HAS INDICATOR 4 |
| INDICATOR 6 |

Any account not meeting the level 1 criteria and having the tenth indicator is categorized as meeting level 2 criteria and provided a score of 4, steps 388, 402. Any remaining accounts are scored based on the level 3 criteria, step 404. Each account is compared to the level three criteria. For all the level 3 criteria that the account meets, the corresponding point values as shown in Table 4 are summed.

TABLE 4

| LEVEL 3 CRITERIA | POINT VALUE |
|---|---|
| INDICATOR 1 | 1 |
| INDICATOR 2 | 1 |
| INDICATOR 3 | 1 |
| INDICATOR 4 | 1 |
| INDICATOR 5 | 1 |
| INDICATOR 9 | 1 |
| INDICATOR 7 | 3 |

To illustrate, an account meeting indicators 1 and 2 is provided a score of 2. If an account meets none of the level 1, 2 or 3 criteria, it is provided a score of 0, indicating that the account is most likely difficult to resolve, requiring an auditor with a high skill level.

Figure 25A:
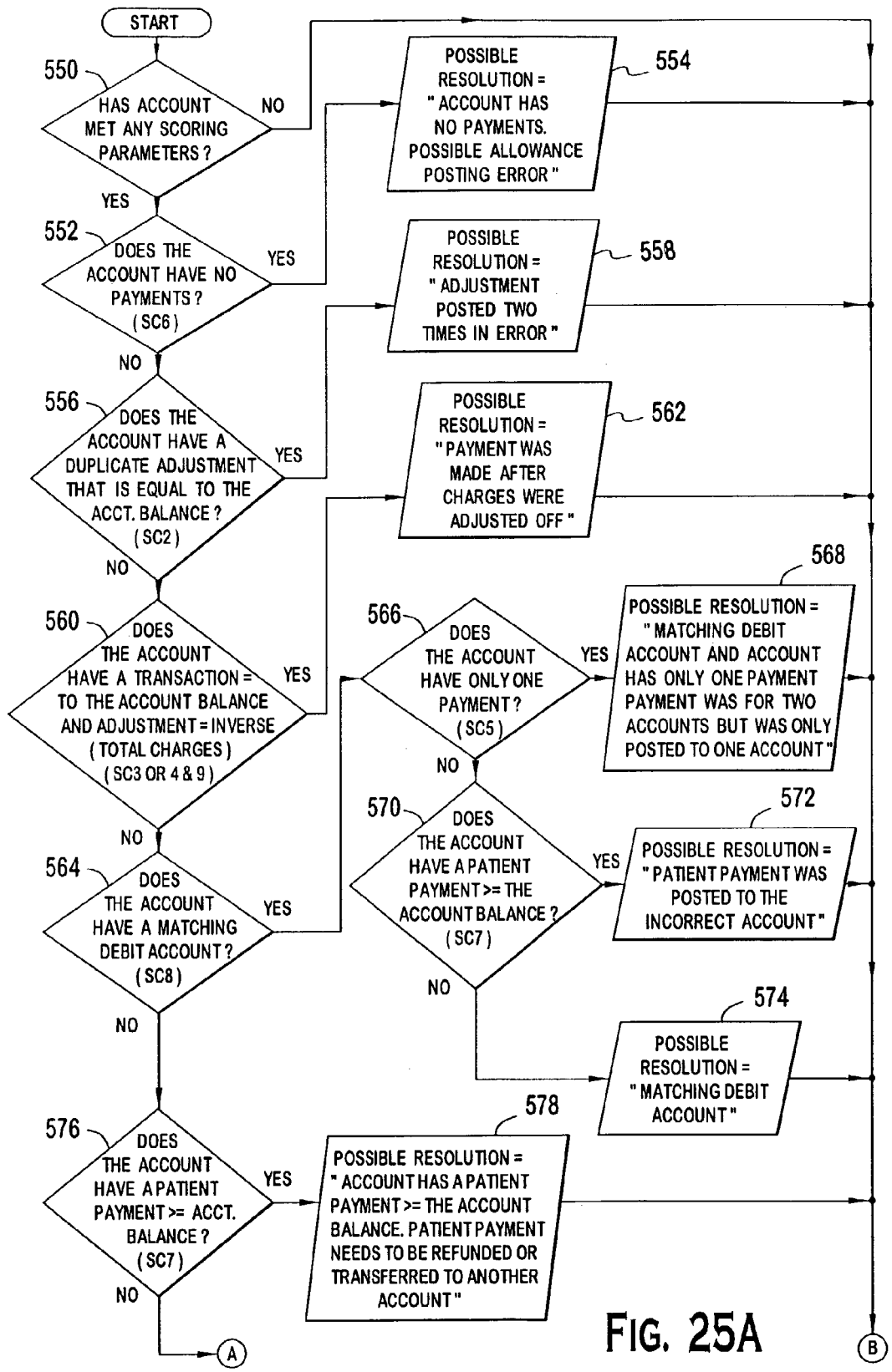
FIGS. 25A and 25B are a preferred flow chart for possible account determination.
Figure 25B:
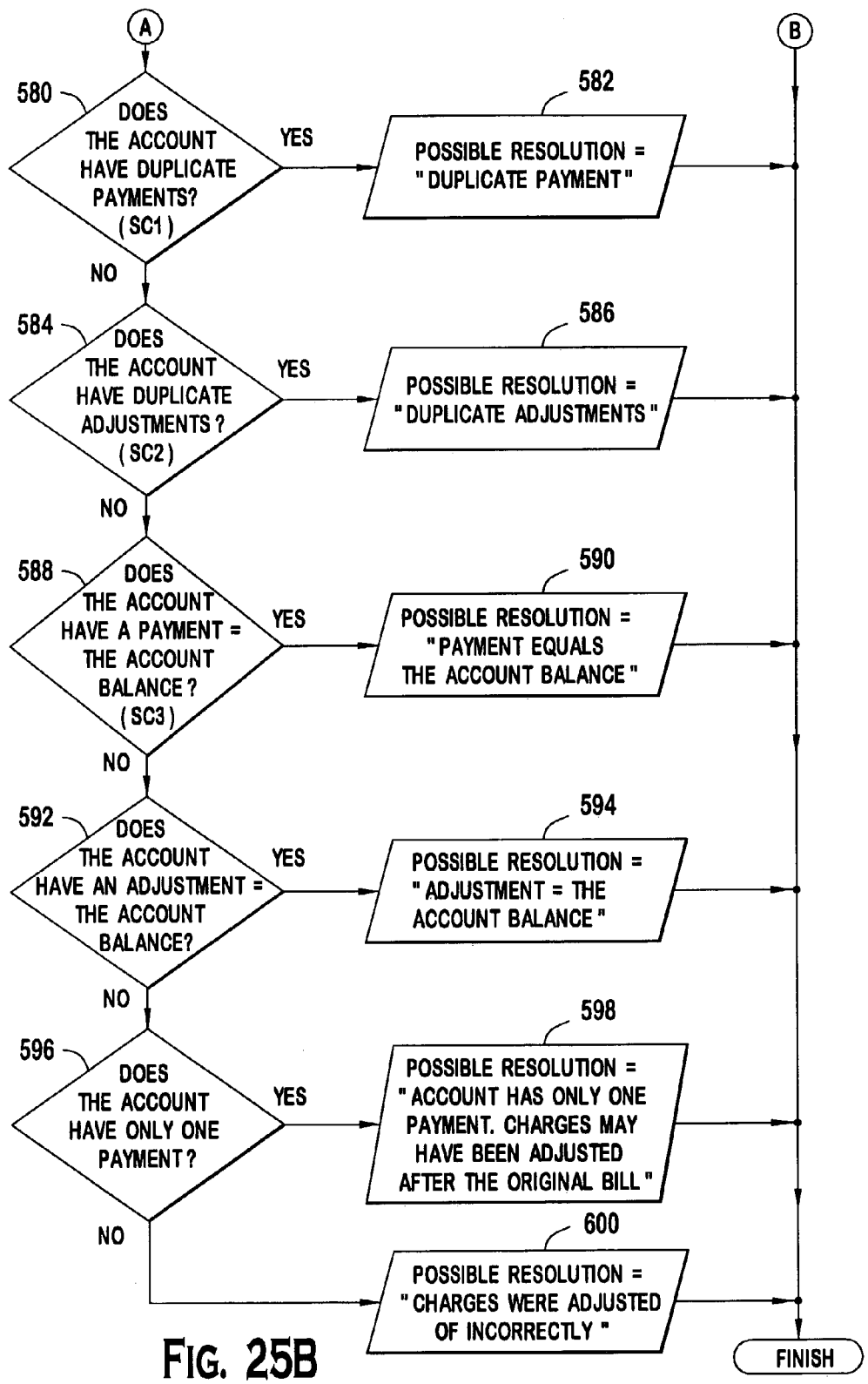

The possible resolution module uses the scoring parameters to determine factors that may have resulted in the overpayment. The factors are presented to the adjuster in a short description, preferably along with the displayed financial details, to aid the adjuster in resolving the account. A flow chart of a preferred resolution determination is shown in FIGS. 25A and 25B.

Initially, the account is checked to determine whether it is associated with any scoring parameters, step 550. If it is not, the problem with the unresolved account is most likely not one of the common problems and no short description is displayed to the adjuster.

If the account is associated with any of the scoring parameters, the account is checked to determine whether it has no payments (scoring indicator 6), step 552. An account having no payments is likely an allowance posting error and the adjuster is preferably provide with a short message, "Account has no payments—Possible allowance posting error", step 554.

If the account has a duplicate adjustment that is equal to the account balance (scoring indicators 2 and 4), an adjustment was likely posted twice, step 556. The adjuster is preferably provided with a short message, "Adjustment posted two times in error", step 558.

If the account has a transaction with an amount equal to the account balance (scoring indicator 3 or 4) or an adjustment equal to the inverse of the total charges (scoring indicator 9), a payment was likely made after the charges were adjusted, step 560. The adjuster is preferably provided with a short message, "Payment was made after charges were adjusted off", step 562.

If the account has a matching debit account (scoring criteria 8), step 564, the account is also checked to determine whether it has only one payment (scoring criteria 5), step 566. If such an account has only one payment, the adjuster is preferably provided with a short message, "Matching debit account and account has only one payment—Payment was for two accounts but was only posted to one account", step 568. If such an account does not have only one payment, the account is checked to determine whether it has a patient payment greater than or equal to the account balance (scoring indicator 7), step 570. If it does, it is likely that the payment was posted to an incorrect account and a short message, "Patient payment was posted to the incorrect account", step 572. If it does not, the adjuster is only provided with the preferred message, "Matching debit account", step 574.

If the account has a patient payment greater than or equal to the account balance (score indicator 7), the payment likely needs to be refunded or transferred to another account, step 576. The adjuster is preferably provided with a short message, "Account has a patient payment greater than or equal to the account balance—Patient payment needs to be refunded or transferred to another account", step 578.

If the account has duplicate payments (score indicator 1), step 580, the adjuster is preferably provided with a short message, "Duplicate Payment", step 582. If the account has duplicate adjustments (score indicator 2), step 586A, the adjuster is preferably provided with a short message, "Duplicate adjustments". If the account has a payment equal to the account balance (score indicator 3), step 588, the adjuster is preferably provided with a short message, "Payment equals the account balance", step 590. If the account has an adjustment equal to the account balance, step 592, the adjuster is preferably provided a short message, "Adjustment=the account balance", step 594. If the account only has one payment, the adjuster is preferably provide with a short message, "Account has only one payment—Charges may have been adjusted after the original bill", step 598. If the account had scoring criteria and did not meet any of the previous criteria, the adjuster is preferably provided with the short message, "Charges were adjusted incorrectly", step 600.

Figure 26:
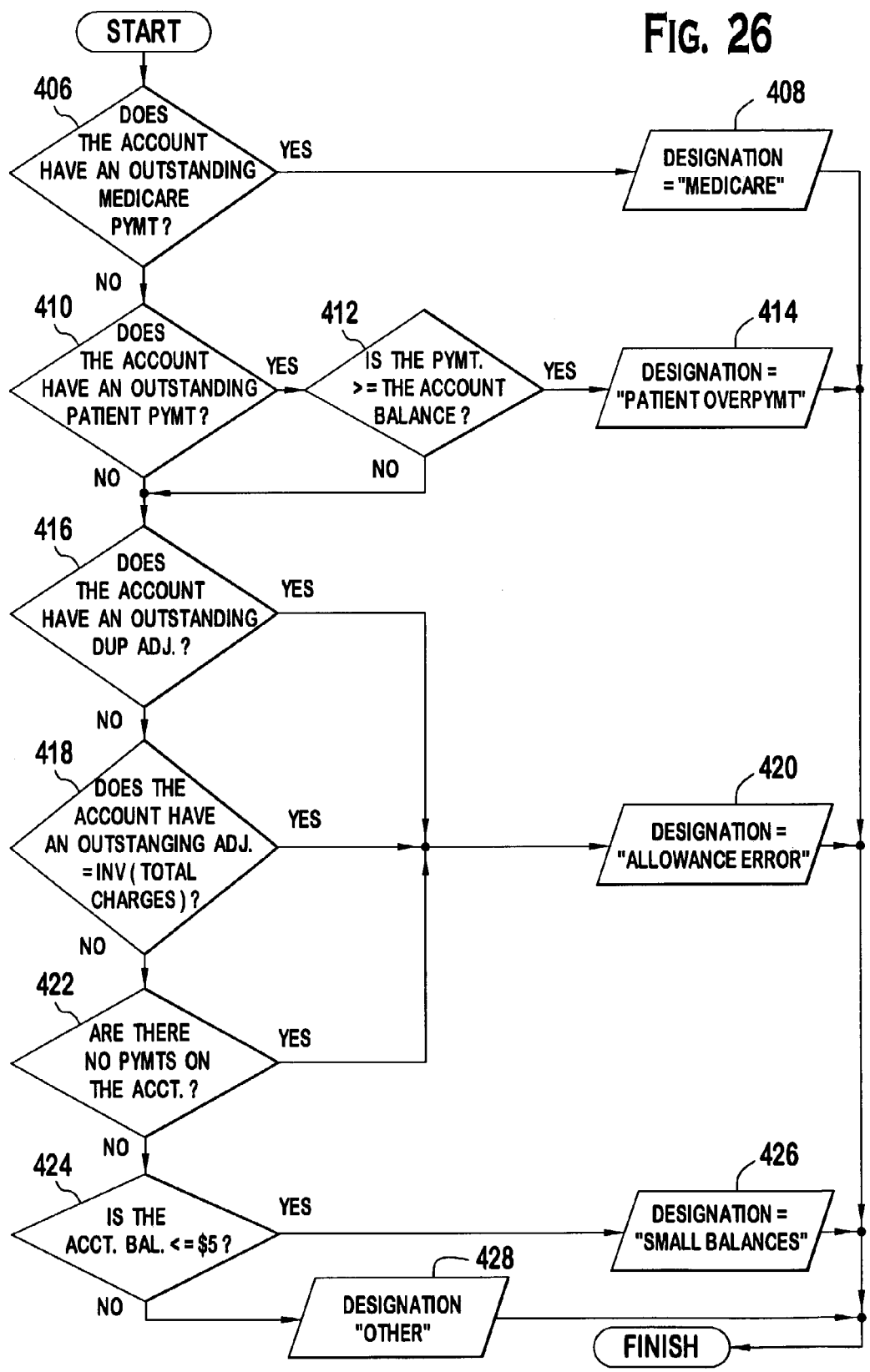
FIG. 26 is a preferred flow chart for designating an account.

To aid an adjustor to handle an account, each account is assigned an account designation as illustrated in the flow chart of FIG. 26. The account designation is preferably displayed on the payment screen on the presentation screens. The preferred account designations are: "Medicare", "Patient Payment", "Allowance Error", "Small Balance" and "All Others".

Initially, each account is analyzed to determine whether it has any outstanding Medicare payments, step 406. The account is checked to see if any Medicare payments were received on the account. These payments are identified by the service code associated with the transaction and are marked as Medicare transactions. If any of an account's transactions are Medicare transactions, the account table is marked to indicate that this account has Medicare payments, step 408. Since each account is analyzed during the scoring procedure, the marking of Medicare payments is preferably performed during scoring. Any accounts having an outstanding Medicare payment is provided an account designation of "Medicare".

If the account is not designated as a "Medicare", it is checked to see if it has scoring indicator 7, steps 410, 412. If the account has indicator 7, it is designated as a "Patient Payment". If the account does not meet any of the prior designation, it is checked to see if it has scoring indicators 4, 2, 6 or 9, steps 416, 418, 422. If the account has any of those indicators, it likely has an allowance error, step 420. Accordingly, the account is designated as an "Allowance Error".

If the account does not meet any of the other designation and has a balance less than a specified monetary amount, such as $4.99, it is designated as a "Small Balance", steps 424, 426. Otherwise, the account is provided a catch-all designation of "All Others", step 428.

Figures 27, 28:
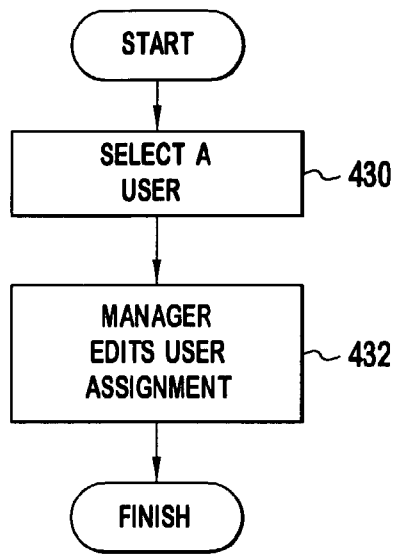
FIG. 27 is a preferred flow chart for assigning an account.
FIG. 28 is an illustration of a preferred workload estimation report.

The account assignment tool allows a manager to effectively assign accounts to users as shown in the flow chart of FIG. 27. The assignment tool stores for each user the accounts assigned to the user. When the user resolves an account, that account is removed from the user assignment.

To assign accounts, the manager selects a user from a list of users for such an assignment, step 430. A screen is displayed indicating the number of accounts assigned to the user. If the manager desires to change the users' current assignment, the manager preferably has the ability to edit by removing and adding assignments to the users list of current assignments. Step 432.

To aid the manager in assigning new accounts, the manager is preferably provided with three quick fill options. These quick fill options are preferably selectable buttons on the GUI. The first quick fill option is for "Potential Medicare Overpayments". By selecting the "Potential Medicare Overpayments" option, the user is assigned accounts having the account designation of "Medicare". These accounts have at least one Medicare payment.

A second quick fill option is "Profit Maximizer". The "Profit Maximizer" option assigns accounts to the user having an account designation of "Allowance Error". These errors, indicators 4, 2, 6 and 9, typically result in an under reporting of revenues for the health care facility. Accordingly, assigning accounts using the "Profit Maximizer" option tends to increase the health care facilities reported profits.

A third quick fill option is "Potential Patient Overpayments". This option assigns accounts to the user having an account designation of "Patient Payment". These accounts, having indicator 7, likely have a patient over payment.

The account assignment tool also allows the manager to assign accounts by querying the patient account application server database. A preferred query screen has three columns. The first column is the search field. Preferably, the search field is selected by a pull down menu, which contains the fields: "Patient Name", "Account Balance", "Date of Service", "Financial Class", "Score" and "Account Designation". The second column is for the operator. Preferred operators are "greater than", "greater than or equal to", "equal to", "less than or equal to" and "less than". The third column is for the value, such as text or numeric. To illustrate, a manager may wish to search for accounts having a "Score" (column 1) "equal to" (column 2) "5" (column 3). Next to the third column is an "Options" link that will preferably provide the user with a specific list of valid values for column 2 or an explanation of the valid values.

For more advanced queries, rows of the preferred screen are combined, such as by using "and", "or", "exclusive or" and "not" operators. To illustrate, a manager may wish to find accounts having a "Score" equal to 5 and not a "Small Balance". Such a query would have a first row of "Score" (column 1) "equal to" (column 2) "5" with a connector of "not" to the second row of "Account Designation" (column 1) "equal to" (column 2) "Small Balance" (column 3).

The "TEST" button is used to check (test) the input parameters. After executing the "TEST" button, the number of accounts that would be assigned to the user is displayed. The "TEST" button also verifies the data as described subsequently.

After all the accounts for a query are retrieved, the accounts are preferably checked to verify that they are not checked out or currently assigned to another user. The results of the search are displayed to the manager. After the assignment is verified, the manager can assign these accounts to the user.

The account assignment tools allow a manager to control the user workload using a workload estimation report. To derive the workload estimation report, an estimated average time period to resolve each account is determined. A preferred time estimator user the account designation and the score to estimate the average time to resolve an account. A preferred table for estimating the time in minutes for a single account having a particular designation and score is per Table 5.

TABLE 5

| DESIGNATION | SCORE | | | | | |
|---|---|---|---|---|---|---|
| | 0 | 1 | 2 | 3 | 4 | 5 |
| Medicare | 10 | 8 | 6 | 4 | 2 | 1 |
| Patient Payments | 5 | 4 | 3 | 2 | 1 | 1 |
| Allowances | 2 | 2 | 2 | 1 | 1 | 1 |
| Small Balances | 1 | 1 | 1 | 1 | 1 | 1 |
| All Others | 10 | 8 | 6 | 4 | 2 | 1 |

Using the average amount of time to resolve an account, a workload estimate for unresolved accounts can be determined. The workload estimation report shows the estimated time expected to resolve the unresolved accounts by their designation and score.

FIG. 28 is an illustration of a preferred workload estimation report. As shown for the preferred report, the designation of account and the score is shown in the left column. The number of accounts in each designation having a particular score are listed in a second column from the left. The average time, in minutes, to resolve each of these types of accounts is in the third column. The total for that score/designation combination is in the fourth column in minutes and the fifth column in hours. The totals are derived by multiplying the total number of accounts for a score/designation combination by the average estimated time to resolve that account. Along the bottom of the report is preferably total for the number of accounts, the total time required in minutes and the total time in hours.

Using this report, a manager has more detailed information to better allocate the manager's user resources. To illustrate, if a Medicare report is due at the end of the month, the manager can determine whether overtime or hiring additional users is required to resolve these accounts.

The system of the present invention preferably includes a report generation module. This report module allows reports to be generated, as needed, to assist hospitals in the management of credit balance accounts. These reports are generated using data collected during the processing of patient accounts. By monitoring system usage and collecting adjuster data, the system can generate reports on staff productivity, system usage, refunds and allowances processed by an adjuster, transaction reports, and fraud exception reports.

There are preferably at least four report categories: audit reports, management reports, profit reports and administrative reports. The audit reports are preferably available for all adjusters to generate specific reports. The audit report allows an adjuster to view transactions related to a specific health care provider.

When the adjuster enters the audit report section, they are preferably asked to provide the name of the health care provider of interest and the date range for transactions for that provider. One method of entering the appropriate selections into the system involves using a drop down menu system.

A drop down menu system preferably includes a drop down menu of providers associated with an adjuster's account (an adjuster's account may include many separate patient accounts). If a specific selection is not made by the adjuster, the provider drop down menu defaults to all of the providers associated with the adjusters account.

The dates of interest are preferably entered in a Batch Date field which is preferably subdivided into Begin Batch Date and End Batch Date fields. Once the provider and date range have been entered, the search can be submitted to the system. Once the search has been submitted, the reports will be generated based on retrieved information that falls within the date range of interest. If the date range is left blank, the report will preferably include all transactions performed by the adjuster involving the provider of interest.

Once the transactions involving a desired provider during a specific date range are identified, the adjuster can generate reports detailing one of many variables of interest. Some, but not all, of the variables that can be used to prepare the report are: Insurance Priority Changes, Possible Errors, Transaction Report, Summary of Refunds, and Summary of Transactions. Once the user selects the desired variable to use to prepare the report, the appropriate data is sent to the Report building Module. The Report Module retrieves the appropriate data and template, and then generates the desired report.

It is preferable that the amount of detail included in a report is customized depending on the particular person requesting the report. For example, if the requester is an adjuster, the data returned will be based on the patient accounts and audit transactions for which the adjuster is responsible. If the requester is a manager, then it is preferred that all transactions involving the selected provider and occurring within the date range is retrieved and included in the report.

While the above mentioned reports are detailed below, the present invention is not limited to such reports. Those of ordinary skill in the art will appreciate that the system can be used to generate any desired reports based on data that is collected by the system. As such, the system can be customized to generate reports that are a combination of the reports described herein.

The possible errors report retrieves account level details of accounts that may contain audit errors and formats them in an easy to read spreadsheet which makes reviewing refund information easy. The transaction report details each transaction code, amount and audit explanation for each account that falls within the desired date range.

The Summary of refunds report summarizes refunds by audit, payer, number of refunds and total dollars refunded for a particular batch or range of batches. The Summary of transactions report summarizes transactions by type, audit and amount for a particular batch or range of batches The Insurance Priority Changes report will retrieve information on any insurances that had priorities changed based on the search criteria. The report will display the patient name, account number, insurance name, original priority code, new priority code, and date.

The Calculator Data report will provide the user with the data associated with the saved calculator. The report will provide the patient name and account number, plus all the fields from the Calculator module. The report will be set up to print the calculator data for each account on a separate page.

Refund Requests that do not allow printing need to be handled differently, such as submitted through an online Payer System. In these cases, the user needs a report that will provide them with the necessary information to enter the data into these systems. To accomplish this, the Remittance Report was created which will list only refunds that do not get checks issued. This report will have the following fields: provider, provider number, patient, policy number, ICN, admin date, discharge date, payment date, payment amount, refund amount, and reason for refund.

The Refund Worksheet will display all refunds for a particular payer on a patient account with the amounts being totaled to provide an overall refund amount. Each refund worksheet will be printed on a separate page when printed.

The reports module preferably also generates reports customized for use by managers. Examples of such reports are: Productivity Summary Report, Productivity Detail Report, Summary of System Usage, Outstanding Medicare Credit Balances, Summary of Non-audited Accounts, Summary of Medicare Accounts, Workload Estimate Report, New Accounts Report, and Fraud Exception Report, Aging by Status, Time to Resolve Credits, Retraction Request Form, Refund Reports by Payer, and Detail Invoice Report.

When a manager enters the managerial report section of the system of the present invention, they preferably have the option of selecting a managerial report to view. The manger can then click a continue button to be directed to a page with detailed report options.

The detailed options depend on the type of report selected, such as Productivity Summary Report will allow for date ranges, and New Accounts Report will allow for provider selections and date ranges. If a manager is viewing the Audit Reports, there will be an additional search field that will list the associated users for the manager in a list box. The manager can then select several users from the list along with the other search fields to generate a report. The manager can then click the submit button, this will submit the information to the Report Module, which will process the request and return the applicable report.

The Aging by Status report will group the accounts by their current status and the aging status time periods. The aging status time periods are preferably 0-30, 30-60, 60-90, 90-120, 120-180, and over 180 days. For each current status time period there are preferably listed the number of accounts contained in the time period and their total dollar amount. The aging date is preferably based on the current date to discharge date.

The Time to Resolve Credits report will list only audited accounts. The report will list the patient name, account number, account balance, audited date, last credit transaction and calculated number of days to resolve. The days to resolve would be based on the audited date to the last credit transaction. The report would be sorted by account balance, highest to lowest, then patient name. At the bottom of the report will be the average number of days required to resolve accounts.

The Retraction Request Form, Refund Reports by Payer, and Detail Invoice Report preferably all use the same type of search form for building the appropriate report. If one of these reports is selected, the manager will preferably be directed to a page that will have a drop down menu of the providers associated with their account. The manager can select a provider, then click a continue button.

The manager is then preferably directed to a form to refine their report options with the following fields: payer, line of business, begin date, end date, check number, type of recovery, reporting status, and invoice number. The payer field will be a drop down menu populated with payers associated with the selected provider. The line of businesses will be a drop down menu populated with LOBs associated with the payer. The type of recovery will be a drop down menu with the options of all, CBAS audit, and CBAS reporting. The reporting status will have the same options has the Post Refund status, which are No Activity, Approved, Not Approved, Submitted, Need Information, Retracted, Invoiced, and Unrecoverable. After the manager has refined their search, the manager will click the build report button.

The Refund Reports by Payer will preferably be the same report that is currently used in the Data Export module. The Retraction Request Form will preferably list patient information, insurance information, and adjustment information. When the report is printed, each patient record will be printed on a separate page.

The Detail Invoice Report will preferably be broken down by payer and line of business with each invoice printing on a separate page. The Invoice can display the payer, LOB, invoice number, and date. Then, each refund will list separate line items with the provider name, ICN, patient name, account number, admin date, refund amount, and the fee (payable to the entity that administers the system of the present invention).

It is preferred that only managers will have access to the Profit Reports. When the manager enters the Profit Report section there will preferably be a search form with Provider, a date range entry mechanism similar to that described for general reports, and Report Type fields. The Provider field will preferably list providers associated with the manager. The Report Type can have Debit Balances Created and Allowances Posted reports.

The Debit Balance Created report can show audited accounts where the audited balance is greater than zero. This report will preferably have the same fields as the Possible Errors report that is listed under the Audit Reports section.

The Allowances Posted report will preferably have the same fields as the Transaction Report that is listed under the Audit Reports section but will only display those audit transactions selected by a manager.

The reports module of the present invention preferably includes the ability to generate Admin Reports. It is preferred that only administrators will have access to these reports. Two types of reports are preferably built into the system for use as Admin Reports. The two types of reports are preferably System Reports Usage and system Account Access.

When the administrator enters the Admin Report section, they will preferably be provided with a drop down menu type of data entry system for selecting what sort of report to view. The administrator can then click the appropriate icons to direct the administrator to the appropriate search form for the selected report.

The System Reports Usage preferably displays the provider, user, report, and the number of times used. The report can be generated using a search criterion that the administrator will be able to select. The search form may have the following fields: provider, user, report type, begin date, and end date. The provider and user fields may also incorporate drop down menus populated with the providers and users that are associated with the administrator respectively.

The report type is preferably a drop down menu containing all the reports in the CDR Auditing System. Once the administrator has selected the search criteria, they can click the build report button, which will open a pop-up window with the desired report displayed therein.

The System Account Access report preferably provides administrators with information regarding users accessing patient accounts. There can be a search form that the administrator will be able to use to build the criterion for the report. The fields are preferably: provider, user, patient last name, account number, begin date, and end date. The provider and user fields will be drop down menus with the providers and users associated with the administrator being listed. The remaining fields can be text fields to allow the administrator to enter a patient last name, account number, or date range.

After the administrator has selected the search criteria, they can preferably click the build report button, which can open a pop-up window with the report being displayed. The report may provide the following information: provider name, user, patient name, account number, and the access dates.

The system of the present invention preferably includes a Medicare Management module that allows hospitals to streamline their compliance procedures. The Medicare Management module allows entities that use the system of the present invention to reduce and manage the risks associated with maintaining compliance with Medicare's credit balance regulations.

Medicare requires hospitals to report Medicare credit balances quarterly and to develop and maintain documentation which shows that each patient record was reviewed to determine if the credit balance is attributable to Medicare. For simplicity, the specification generally refers to the current form required by Medicare (i.e., the HCFA Form 838). However, portions of the specification as well as the claims refer to the required report as a Medicare Refund Compliance Form. Those of ordinary skill in the art will appreciate from this disclosure that the term Medicare Refund Compliance Form refers to the HCFA Form 838 or any later form(s) developed by Medicare for reporting credit balances. The Medicare Management module of the present invention provides the first automated tool that is available to hospitals today to assist in meeting and managing the Medicare credit balance reporting requirements.

The Medicare Management module of the present invention enables multiple techniques to be used to manage Medicare credit balance accounts. One tool provided by the Medicare Management module is a Medicare Account Identifier. This tool analyzes outstanding payments on each account to determine if a potential liability to Medicare exists. The Medicare Management module preferably places a Medicare identifier on each account that is used in the Medicare Workload Estimate and user account assignment, as well as Management Reporting.

The Medicare Management module preferably also includes a Medicare Refund Tracker function. When a Medicare account is identified and determined to represent a payment due to Medicare, the Refund Tracker function records and follows the manipulation of the account from identification through the reporting to Medicare and through the transfer of funds to Medicare. The Medicare Management module of the present invention provides a clear systematic audit trail of identified Medicare refunds for hospitals that was never available before.

The Medicare Management module preferably includes an Automated HCFA 838 function. Every hospital is required to submit quarterly reports to HCFA, the agency that monitors Medicare credit balances, detailing all of the Medicare overpayments identified by the hospital.

The Medicare Management module preferably includes an alert function that automatically notifies a hospital officer (via email) 30 days prior to the due date of the report. The notification preferably includes a calculation showing the estimated manpower necessary to analyze each account. The Medicare Management module notifies the officer again seven days before the due date if the report has not yet been submitted.

The Medicare Management module preferably alerts managers at the end of each calendar quarter and one week before the 30-day deadline for submitting the report. In addition to the above described email alerts, another alert will preferably occur when managers login to the System of the present invention. Each time a manager logs in, the date will be checked to determine if it is within the 30-day grace period of a new quarter. If it is, then the system will check to see if the corresponding Form 838 has been submitted for the previous quarter. If the form has not been submitted, the manager will receive a pop-up alert upon initial login and an alert notice will be displayed on the main entry page throughout the manager's session.

In addition to providing reminders to hospital officers, the Medicare Management module can preferably automatically complete the HCFA Form 838 by identifying all accounts managed by the system of the present invention and listing any audited accounts that have payments due back to Medicare. It is preferable that the Medicare Management module uses the information generated through the Calculator module and the Account Resolution Process module to populate the HCFA 838. The Medicare Management module also takes advantage of its integrated systems to provide the value codes required by Medicare on the HCFA 838. The value codes are generated by translating the refund explanations (discussed above in connection with the automated hospital forms) to the HCFA reason and value codes required by Medicare.

The Medicare Management module preferably automatically retains copies of prior HCFA 838 Reports. Once a report is submitted to Medicare it is preferably locked out so that changes to the report cannot be made afterwards. The retention of actual copies of prior reports greatly simplifies compliance procedures for any future audit requirements.

The Medicare Management module preferably allows managers to update and print out interim reports detailing Medicare refunds. When the manager enters the Medicare Refund Tracker function, he or she is preferably presented with a search form. The form is preferably configured to receive search criteria via a drop down menu system. However, any method of entering the search criteria can be used without departing from the present invention. Some of the criteria that can be used is: the providers that are associated with the manager; a date range; refund status, either non-submitted or submitted; or the like. The manager can then submit the completed search form and the Refund Tracker function searches the database to return the Medicare refunds that match the criteria.

The date range search will preferably be based on when the refund was batched, not the submitted date. This is important because the refunds that are used on the Form 838 are based on refunds batched during the calendar quarter. A manager will still be able to retrieve Medicare refunds from other quarters that have not been completely processed, but any updates will not alter the Form 838 that was submitted.

For each identified Medicare refund, the system will preferably display the following information: patient name, policy number, admit date, payment date, payment amount, and refund amount. If the selected refund status was non-submitted refunds, then next to each record will be a set of checkboxes. One will be for submitted refunds and the other for the refund fulfilled. This will allow for managers to update multiple Medicare refunds at one time.

If the manager wants to view the refund details on a particular patient listed, the patient name is preferably linked to allow the adjuster to view detailed information on the selected refund. The refund detail page will preferably have the patient name, policy number, provider name, provider number, ICN, admit date, discharge date, payment date, payment amount, refund amount, and refund reason. The detail page will also preferably have the two check boxes for marking a refund as submitted and/or fulfilled. The adjuster can select the appropriate boxes then click the submit button. The information will be saved and the adjuster will be returned to the refund details page. To return to the search results page, the user will be able to click the back to results button.

If a refund has been entered into the Medicare terminal, then the manager will check the submitted checkbox for that record. If a check has been sent for the refund, or if Medicare has deducted the overpayment from a remittance advice, then the refund fulfilled checkbox can be selected. If this checkbox is selected and the submitted checkbox has not been checked, the submitted checkbox will be automatically checked. Once all applicable refunds have been checked, the manager will click the submit button. This will update the appropriate Medicare refunds, and then return the manager to the search results page, with the selected refunds no longer present. If the refund status selected was submitted refunds, then only refund fulfilled checkboxes will be available to the managers.

The managers will preferably also be able to print a report provided by the Medicare Refund Tracker function by clicking the print icon or the like. This will cause a pop-up window to open with the appropriate Tracker report, without checkboxes, to be displayed. This will allow the form to be printer friendly. To print the form, the manager can use the browser print function.

As detailed above the Medicare Management module preferably allows the manager to prepare and process the Medicare Form 838. When the manager enters the section for Medicare Form 838, there will is preferably a drop down menu of providers associated with the manager and a drop down menu for choosing a calendar quarter and year that will be used to retrieve the Form 838. The drop down for quarter and year will be populated based on the date that the selected provider's account was created. This will allow managers to retrieve Form 838s whether the form has been submitted or not. There is a field to the Medicare Form 838 search form that is a drop down menu with Inpatient and Outpatient options.

To start, the manager will need to select the type of Medicare Form 838 that is to be viewed or edited. When the manager clicks the search button, the database will be checked to determine if Medicare Form 838 has been submitted or not. A submitted Medicare Form 838 will retrieve the appropriate data from the database. A non-submitted Medicare Form 838 will compare the provider account types to the patient account types and return the appropriate information to allow the manager to edit Medicare Form 838. If the Inpatient option was selected, then the Medicare Form 838 Medicare Part field will be marked as "A" as shown in FIG. 29A. If the Outpatient option was selected, then the Medicare Form 838 Medicare Part Field is marked as "B" as shown in FIG. 29B.

If the 838 form does not exist in the database, then that calendar quarter has not had a Form 838 filled out and submitted to Medicare. This will result in the managers being directed to a Form 838 with the applicable information entered and the managers will have the ability to edit various fields for each record. This form would preferably be for the most recent quarter that a Form 838 was not submitted and that has Medicare refund data.

The Form 838 has standard fields that must be entered and there are two fields that preferably have the proper option automatically selected based on posted refund information. These two fields are the Reason for Credit Balance and Value Code. Because this form will be tied into the system of the present invention, many of the fields will be automatically populated and cannot be edited. Below is a preferred list of fields on the form and whether the field can preferably be edited.

Provider Name—Pulled from the System of the present invention

Provider Number—This will be a form field for the manager to enter a value

Quarter Ending—This will be based on the quarter selected from the previous page Medicare Part—Based on whether the user is submitting IP or OP claims Page Number—Automatically generated based on the current page and total number of pages Contact Person—This will be a form field for the manager to enter a value. Defaults to name of manager.

Phone Number—This will be a form field for the manager to enter a value. Defaults to phone number of manager.

Beneficiary Name—Pulled from the System of the present invention, the patient name HIC Number—Pulled from the System of the present invention, the policy number ICN Number—Pulled from the System of the present invention, the Medicare Internal Control Number Type of Bill—This will be a drop down menu with a list of three-digit numbers to indicate the type of billing. The numbers will be standardized for this form.

Admission Date—Pulled from the System of the present invention, the admit date

Discharge Date—Pulled from the System of the present invention, the discharge date Paid Date—Pulled from the System of the present invention, the payment date Cost Report—Pulled from the System of the present invention, based on admit date to end of quarter. If less than a year, then OPEN; greater then a year, CLOSED Amount of Credit Balance—Pulled from System of the present invention, refund amount Amount Repaid—This will be a form field for the manager to enter payment amount being submitted with the submission of Form 838

Method of Payment—This will be a drop down with options for selecting "C" for checks or "A" for adjustment. Defaults to "A"

Medicare Amount Outstanding—Automatically calculated by subtracting Amount Repaid from Amount of Credit Balance Reason for Credit Balance—will be a drop down menu with the following numbers 1, 2, and 3. The number corresponding to the note reference primary code will automatically be selected.

Value Code—will be a drop down menu displaying the available two digit codes, which currently are 12, 13, 14, 15, 16, 41, 42, and 43. If the note reference selected for the refund transaction has the value code entered, then the corresponding value code will be selected. There will also be a blank option if no code should be selected or if the note reference value code does not match the current list of value codes.

Primary Payer & Address—Pulled from the System of the present invention, the COB information At the bottom of the 838 form there are preferably three functions that can be selected to update, print, and submit the 838 form. If the manager clicks the update function, the form will be validated. The validation of the 838 form preferably consists of checking the updated provider number, contact person, phone number, and amount repaid being entered, and calculation check of the Medicare Amount Outstanding. If any of these checks fail, the manager will be alerted with the option to submit the update or cancel the update to correct the potential error.

If the manager selects to submit the updates with potential errors, the data will be saved to the database and the manager will be returned to the form. If the manager selects to print the form, a pop-up window will preferably open with the form being displayed without the editing features.

If the manager has completed filling out the form and is ready to submit the form to Medicare, the manager can select the submit function. The manager will receive an alert once a form is submitted indicating that the form can no longer be edited. Once the manager acknowledges this alert the form will be validated. If errors are still present at this time, the form will not be processed. If the validation is successful, the form will be saved to the database and marked as submitted. The manager will preferably then be directed to the form with no editing features and a pop-up window will open with the Report Certification letter and Form 838 being displayed. The manager can then print the report for submission to Medicare. Under the Management Reports module, there are two reports which are specific to the Medicare process. The Outstanding Medicare Credit Balances and Summary of Medicare Accounts reports are available on demand.

Figure 30:
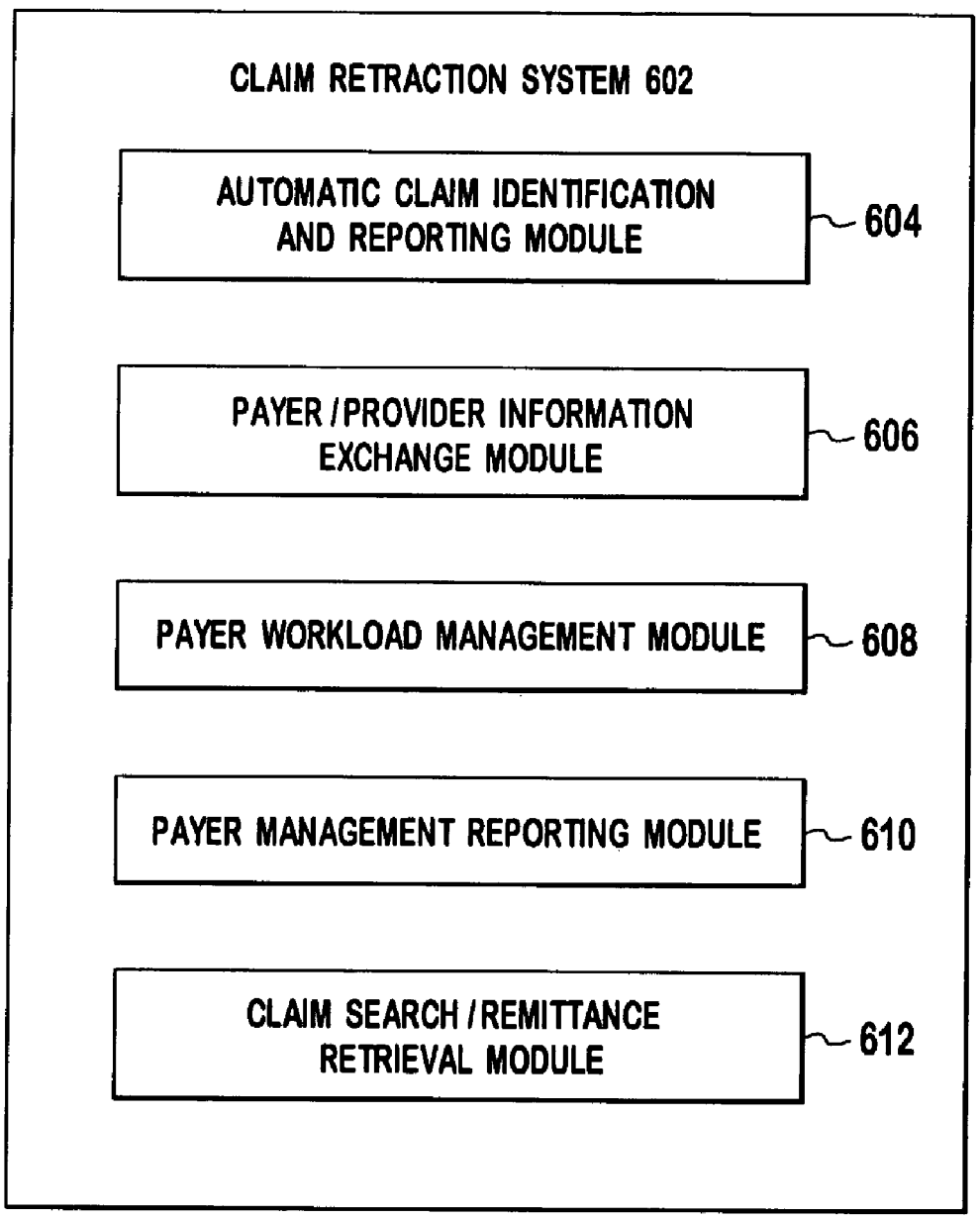
FIG. 30 is an illustration of a claim retraction system.

The preferred payer (insurance companies) software enables the electronic identification, recordation, posting and reporting of retracted claims between providers (health care facilities) and payers (insurance companies). Typically, the provider and the payer systems use different fields. To facilitate communication between the two systems, the claim retraction system acts as a bridge between the two systems. As shown in FIG. 30, the claim retraction system 502 has five components: an automatic claim identification and reporting module 604, payer/provider information exchange module 606, payer workload management module 608, payer management reporting module 610 and claim search/remittance retrieval module 612.

Figure 31:
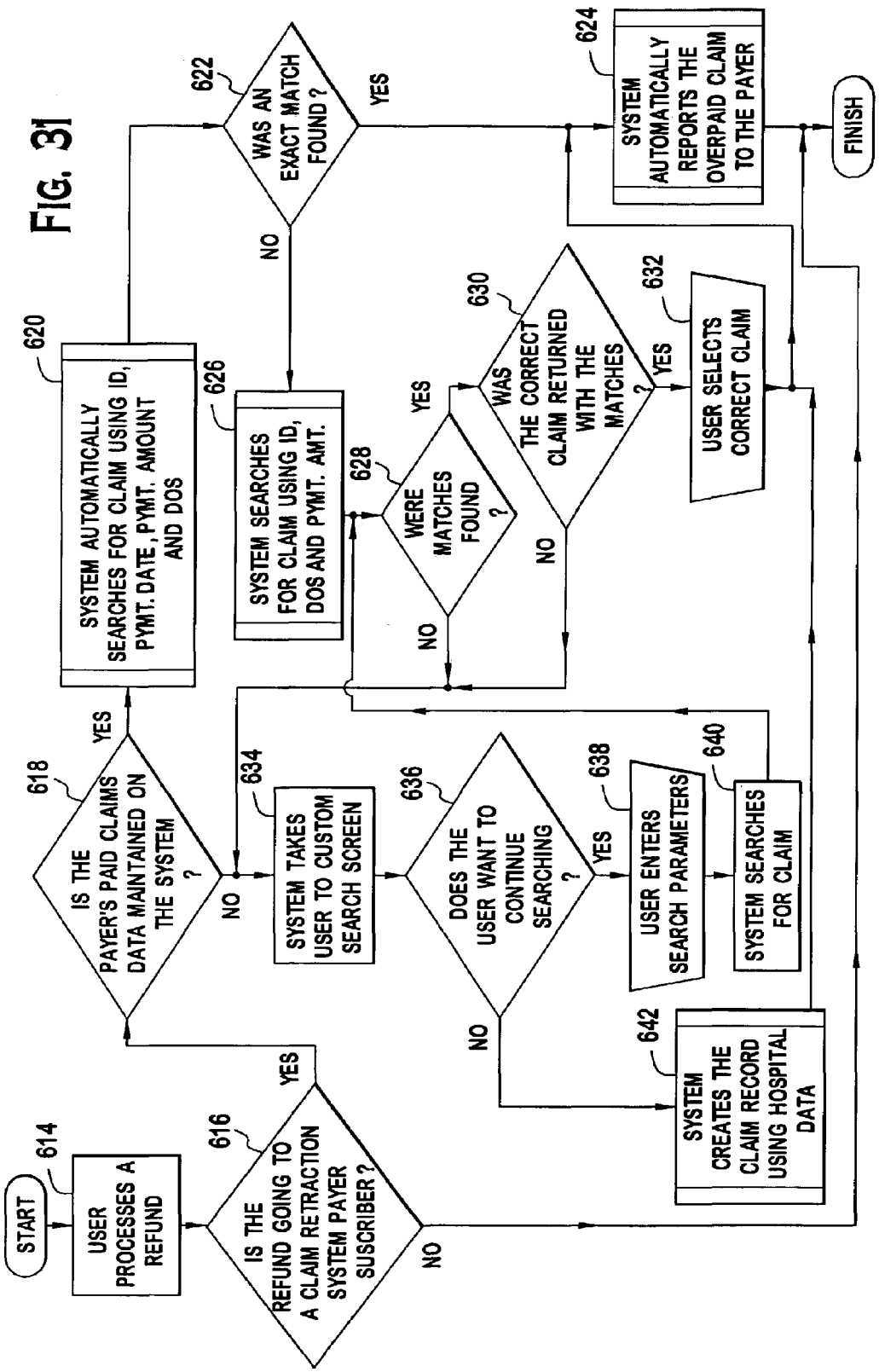
FIG. 31 is an automatic claim identification and reporting system flow chart.

The automatic claim identification module 604 is explained in conjunction with the flow chart of FIG. 31. The reporting module 604 allows, if all the claim data is available, for an automatic reporting of overpayments to payers. However, if lesser claim data is available, the module 604 allows for a partial automation of the reporting of overpayments.

The overpayments reporting can be divided into four scenarios reflecting the available claim data. In scenario one, the provider and payer claim data is available to the module 604 allowing for a highest level of automation. In a second scenario, the provider data is available to the system and the payer data is not available. In a third scenario, the payer data is available and the provider data is not available. In a fourth scenario, neither the payer or provider data is available.

For scenario one (both provider and payer data is available), steps 616, 618, a link is created between the provider and payer data. When an adjuster (provider user) processes a refund, step 614 an automatic search for the matching claim within the payer claim data is performed step 620. The matching claim is detected using the Subscriber ID, date of service (DOS), Payment Amount and Payment Date from the provider's data. If an exact matching record is found, step 622 the overpaid claim is reported to the payer, step 624.

If an exact match is not found, potential matches are found searching the Payer's paid claims using the Subscriber ID, DOS and Payment Amount, step 626. The adjuster can select one of the potential matching claims and report the overpaid claim to the payer step 628, 630, 632, 624.

If the adjuster does not find a match using the initial search results, the adjuster can use a custom search screen, step 634. The custom search screen allows the user to create custom searches using the following preferred parameters in any combination: Subscriber ID, Subscriber Name, DOS, Payment Amount, ICN or hospital account number. In the preferred implementation, the fields are initially filled with the information retrieved from the Provider refund record. This filled information can be modified by the searcher, step 638. If the search results in the correct claim being discovered, step 640, the overpaid claim is reported to the payer.

If the adjuster is not able to find the correct claim, step 636, a new claim record is automatically created using the provider refund data, step 642. This created record is reported to the payer.

In scenario two (provider data but no payer data), step 618, a new overpaid claim record is automatically created using the provider refund data, step 642. In scenario three (no provider data but payer data), the adjuster searches the payer paid claims file and manually selects the correct claim to report to the payer. The adjuster uses a custom search screen. The custom search screen allows the user to create custom searches using the following preferred parameters: Subscriber ID, Subscriber Name, DOS, Payment Amount, ICN and Hospital Account Number. If the correct claim is discovered, the overpaid claim is automatically reported to the payer. If the correct claim is not found, the adjuster enters the data into a newly created overpaid claim report to be submitted to the payer. In scenario four (no payer or provider data), the adjuster enters the data required to create the new claim report.

The payer/provider information exchange module 606 allows the health care facility (provider) to report each overpaid claim that has been identified by the provider to the payer in a format required by the insurance company (payer). The module 606 also allows the payer to review each claim to determine whether all necessary data elements for the retraction are present. If additional information is required by the Payer, the module preferably sends the provider adjuster a message requesting the additional information. The provider can send the requested information to the payer via the module.

Figure 32:
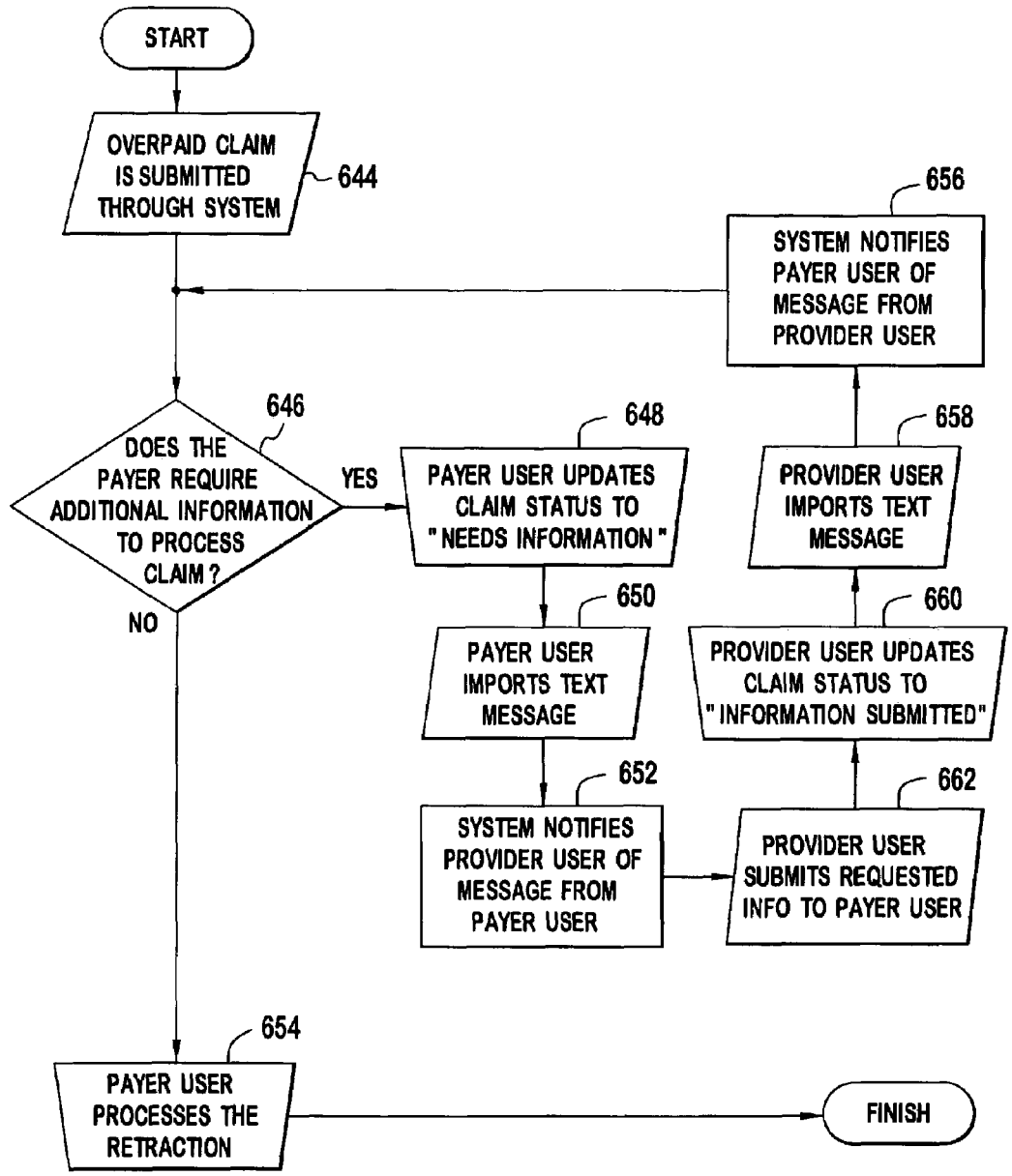
FIG. 32 is a payer-provider information exchange flowchart.

FIG. 32 is a flow chart of a preferred information exchange. Once an overpaid account has been identified by the provider via the account analysis module, if the payer is subscribed to the system, the overpaid account information is sent to the payer in an automated manner, step 644. Preferably, the information submitted to the payer via the module includes date reported, patient name, hospital account number, payer claim number, refund amount and a reason for the over payment. After the payer user reviews the information for an overpaid account, the user can place an indicator of the status of the account. The preferred status indicators are: "In Progress", "Retracted", "Need Information from Provider" and "Cancelled by Payer". The adjuster for the account of the provider can review the status indicator of the account via the system at any time.

For an account requiring additional information prior to retraction, step 646, the payer user sends a text message to the provider adjuster detailing the information request, steps 648, 650. The system queries the accounts at the payer for accounts having the status indicator of "Need Information from Provider". Using the identified accounts, each provider user (adjuster) is provided with a list of accounts and his/her associated text messages, step 652. Preferably, these messages are provided to the user at sign in to the system. When the user signs in, the claims requiring information by the payer are displayed. The adjuster can select a claim and the detailed information of the claim and the text message.

The adjuster, after gathering the requested information, sends a text message to the payer user detailing the requested information, steps 662, 658. The adjuster changes the status indicator of the account to preferably, "Requested Information Sent", step 660. The adjuster is preferably only permitted by the system to change the status only when the reply message is entered.

The system queries the claims for those having the indicator, "Requested Information Sent". Each payer user is provided with a list of claims that the requested information was sent. This list is preferably available the payer user at sign in. The payer user can select an account from the list and view the detailed information and the text message sent by the adjuster. If the information is sufficient to retract the account, the account is retracted, step 654, and the status is changed by the payer user to "Retracted". Otherwise, the user changes the status to typically either, "In Progress" or "Cancelled by Payer".

Preferably, either the payer or provider user can change the status of the account to "Cancelled by Payer" or "Cancelled by Provider", respectively. The user canceling the attempted retraction is required to provide a text message explaining the cancellation. If the claim was cancelled by a payer user, the corresponding provider user is sent the message. If the claim was cancelled by a provider user, the corresponding payer user is sent the message. That user is provided with a list of the cancelled accounts, preferably at sign in. The user can select a cancelled account and view the account's detailed information and the cancellation text message.

Figure 33:
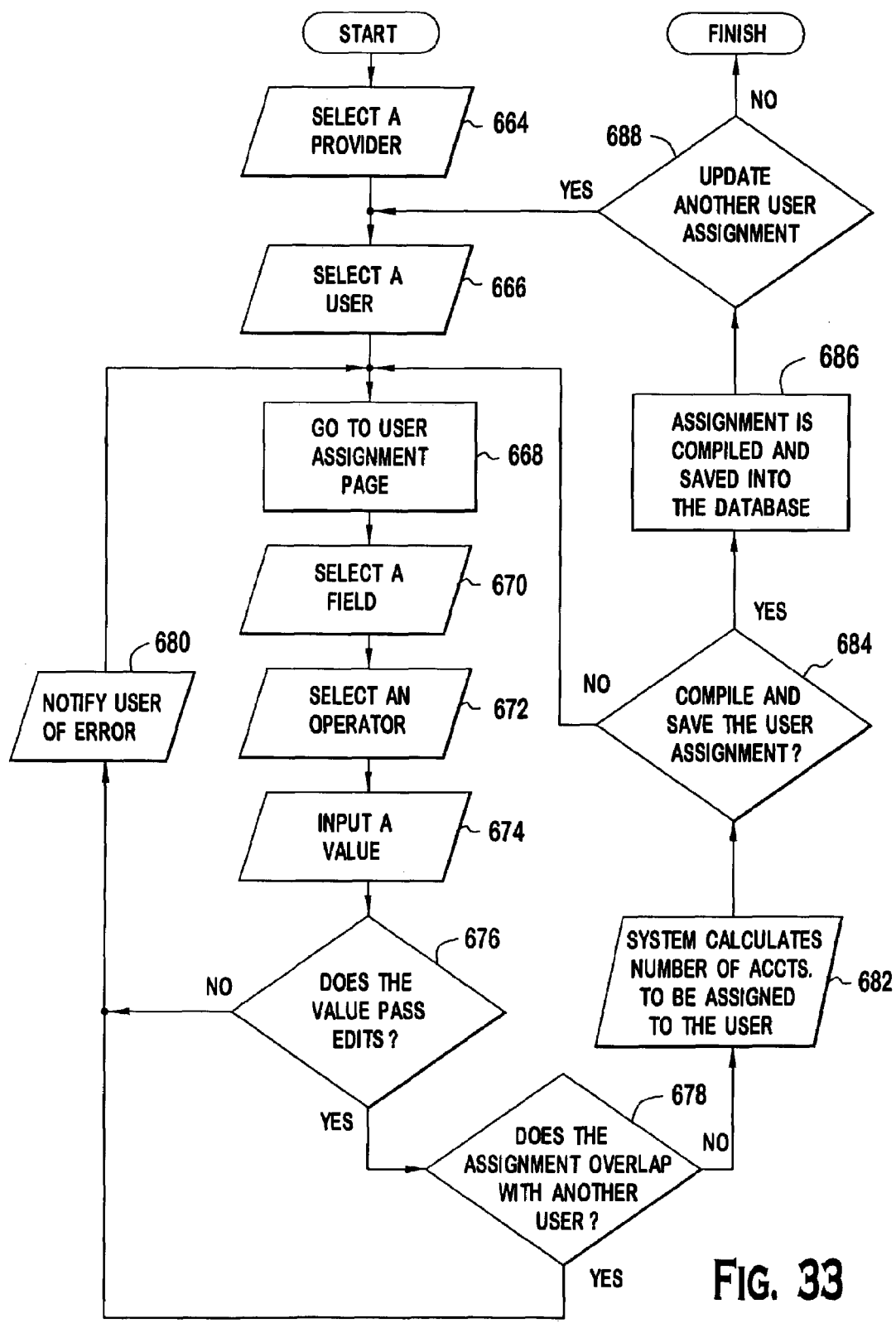
FIG. 33 is a payer workload management flow chart.
Figure 34:
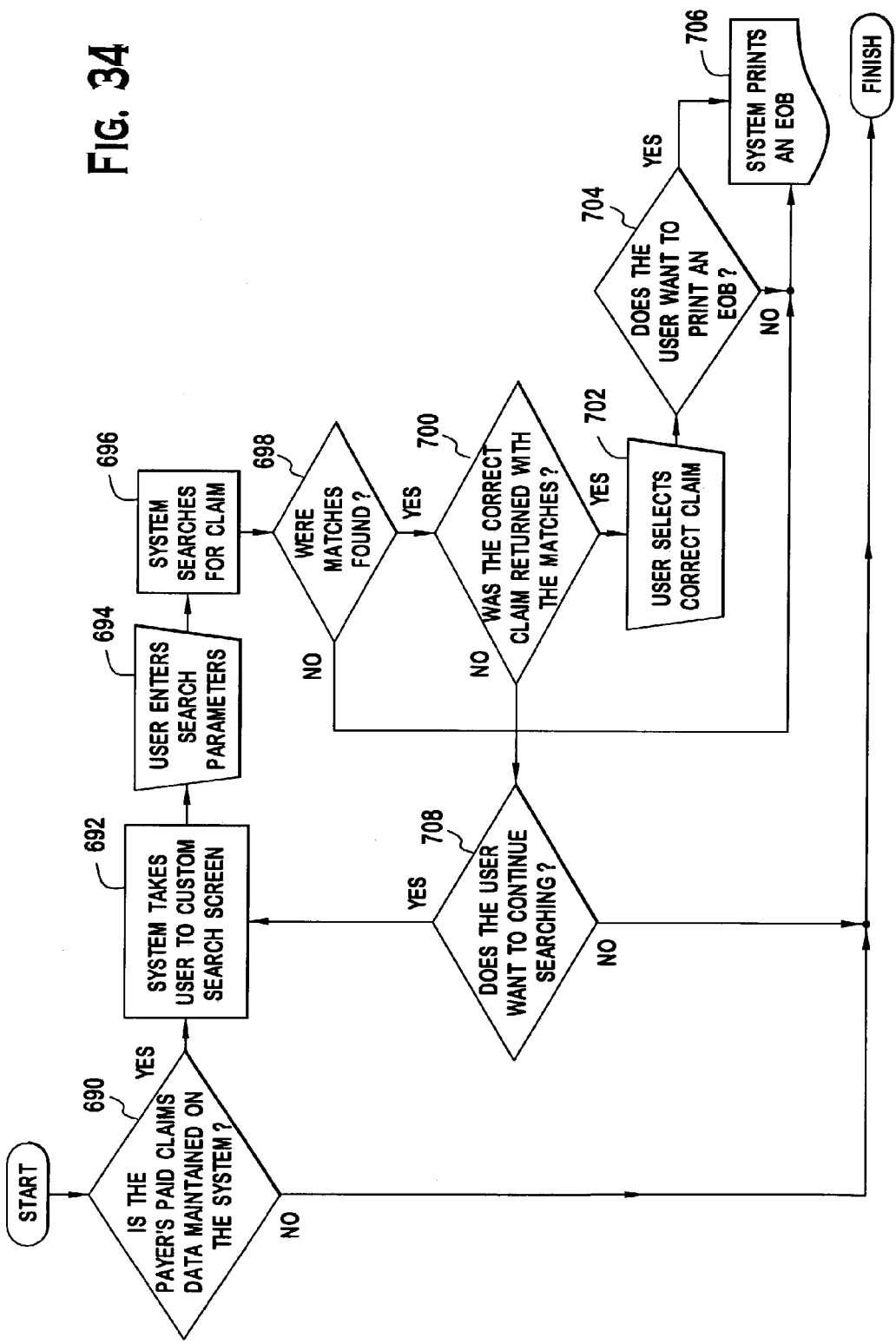
FIG. 34 is a claim search/remittance retrieval flow chart.

The payer workload management module 608 allows for a payer manager to assign overpayment accounts to payer user in an efficient manner. Workload management is described in conjunction with the flow chart of FIG. 33. A user assignment screen is displayed to the manager. The assignment screen has a field allowing the manager to select a particular provider (health care facility) or all providers, step 664, preferably by a pull-down menu. The default entry is preferably all providers.

Based on the selected provider(s), the total number of overpaid accounts for the provider(s), a list of unassigned accounts, and a list of payer users associated with the provider(s) is displayed. Also, displayed for each user is a number of accounts currently assigned to that user. If a particular provider is selected, each payer user assignment of that provider is editable, preferably by executing an edit icon by the manager.

For each user, a user detail page can be displayed showing the total number of accounts assigned to the user and a listing of providers with the user assignment details and account numbers for each provider. Edit icons are preferably displayed next to each provider so that the manager can edit the user assignment.

When the manager edits a user assignment, step 666, an assignment entry page is displayed, step 668. The entry page preferably displays the payer user's name, the provider name, a quick fill button for profit maximizer and assignment variable fields. The profit maximizer button assigns accounts as to maximize the payer's profit. The accounts are assigned in an order based on their business group, line of business and whether or not the groups are self insured. To illustrate, one group serviced by the payer may be self insured and the other group may not be self insured. The resolution of the account for the self insured group is passed onto that group and it does not impact the payer's bottom line. However, resolution of accounts for the non-self insured group improves the payer's bottom line and resolving these accounts first improves the payer's profits. The profit maximizer assigns accounts to users having an allowance error (scoring indicators 2, 4, 6 and 9) first. Retracting these accounts tends to increase the payer's profit.

The assignment variables are broken down into three columns. Preferably, five rows are provided on a the entry page, with a link provided to add five additional rows. The first column allows the manager to select a field to be queried, step 670, preferably selected by a pull-down window. The selectable fields are: patient name (first character of last name), submission date, line of business, provider and group number. The next (second) column is for the operator: greater than, greater than or equal to, equal to, less than and less than or equal to, step 672. The last (third) column is for a query value, step 674. The type of field being queried determines the allowed query values for the third column.

After the assignment variable fields are filled, the system verifies that the information in each row is in the proper data format, step 676. If it is not, an error message is generated, step 680. By executing a test button by the manager, a number of accounts the query results in is displayed, step 682.

After the number of accounts is determined, the system checks the resulting accounts to verify that they are not "checked out" to another user or overlaps with another user assignment, step 678. If the check fails, the manager is provided a reason for the failure.

If the check is favorable, the manager can save the results by executing a "Save" button, step 684. If the save button is executed without the test being previously executed, the system performs the test and results checking automatically. The saved results are saved to a file and the applicable accounts are updated with the payer user identification (ID), step 686. After one payer user assignment is completed, the manager can proceed to assign accounts to another user, step 688.

As the overpaid account data for an account is provided, the system checks the user assignment for the account. If the account matches a user assignment, it is automatically assigned to the user.

The payer management module 610 enables the providers (healthcare facilities) and payers (insurance companies) to access and prepare numerous reports and forms. These reports and forms include refund reports by payer, detail invoice reports and retraction request forms. The module 610 also allows for the creation and storage of custom reports.

The payer manager selects a report or form to be prepared. A provider is selected by the manager, preferably by a pull-down menu. A screen for refining search options is displayed to the manager. The search options field include Payer, Line of Business (LOB), Begin Date, End Date, Check Number, Type of Recovery, Reporting Status and Invoice Number.

The payer and LOB fields are preferably populated by using a drop down menu displaying the payers/LOBs associated with the selected provider. The Type of Recovery field is preferably filled by a drop down menu having options including All, System Audit and System Reporting. A System Audit is an account that is identified by a CDR user (non-health care user) for auditing and a System Reporting is an account identified by a health care facility user. The Reporting Status is preferably a pull-down menu having options: No activity, Approved, Not Approved, Submitted, Need Information, Retracted, Invoiced and Unrecoverable. The Begin and End Date fields are filled with a date or range of dates. The Check Number and Invoice Number fields are filled with a corresponding numeric value or range.

After the report/form generation information is selected, the manager can construct the report/form by executing a Build Report button. The generated report is subsequently displayed to the manager. The manager can print the report or export it to a data file.

The claim search/remittance retrieval module 612 allows provider users to create custom queries to search payer paid claims. The provider user is provided with a display screen having search fields, step 692, including ICN, last name, first name, recipient ID and account number. To perform a search (if the payer's data is on the system, step 690), either at least the ICN or at least two of the other fields must be used. For the last and first name, partial data can be entered and records having a last/first name with beginning letters matching the entered letters is returned. After the search criteria is entered, step 694, the search criteria is checked to see if at least the ICN or two other criteria is included. If the check fails, an error message is displayed. Otherwise, the claims database is queried using the search criteria and the provider numbers associated with the Provider user ID.

The results of the search are displayed, step 698. Preferably, the results are displayed as last name, first name, account number, recipient ID, from date of service, payment date and payment amount. The results are also preferably ordered by last name, then by first name and then by from date of service. If no results are returned, the user can try different criteria, step 708.

A specified number of the results are displayed on a screen. If the results exceed this number, a list of screens is provided the user to navigate through the results. For each record, a report can be viewed or printed by executing a corresponding icon. A detailed claim report is displayed, preferably without graphics to aid in printing. The displayed report includes: last name, first name, account number, recipient ID, ICN, claim status, claim total charges, claim non-coverage charges, claim deductible, claim coinsurance, claim contractual, payer name and provider name. The report can be printed by executing a corresponding print button.

For each record displayed in the search results, the provider user can select the claim for retraction, step 700, 702. Once the correct claim is identified, the user is given the option, step 704, of printing a copy of the paid claim information in the form of a recreated EOB, step 706. The selection can be performed from the displayed search results or from the displayed claim report details. Selecting the claim retrieves a claim retraction form. If the provider user can not find a desired claim in a search, the user can manually enter a new claim.

When the claim is retrieved for retraction, it is "checked out" to prevent other users from also attempting to retract the claim. The claim information that was on the search page results is preferably displayed on the top of the screen along with the retraction form.

The fields in the retraction form are reason for refund, refund amount, COB insurance name, COB insurance number and additional information. The reason for refund is preferably populated by a pull-down menu with notes from the notes reference database. The refund amount is automatically populated with the claim payment amount. The provider enters the information of the other fields. The retraction can be submitted using a corresponding retraction button. After executing the corresponding retraction button, the retraction form is checked to ensure that the reason for refund and refund amount fields are complete and the refund amount is not greater than the claim payment amount. If the check fails, an error message is displayed with the reason for the error.

If the check is successful, the retraction information is saved to a database and the retraction status is marked as "Submitted". The claim is also "checked in". If the claim is not submitted, such as by canceling the retraction, the claim is "checked in" so that another user may retract the claim or resolve the problem.

For all submitted retractions, the manager is provided a list, preferably by email. The email confirms the submission of the retractions along with information for each retraction. The retraction information includes status, submission ID, ICN, refund amount, reason for refund, provider name and payer name.

What is claimed is:

1. A method for determining possible resolutions of patient credit balance accounts, wherein patient credit balance accounts are accounts on a service provider's accounts receivable having financial transactions including cash payments and contractual allowances in excess of total charges and the patient credit balance accounts including information relating to services provided to a patient and accumulation of charges associated with the service, the method comprising:

inputting, for use by a processing device, the patient credit balance accounts and financial transactions associated with the patient credit balance accounts;

identifying, by the processing device, criteria associated with possible resolutions to the patient credit balance accounts in response to the inputted financial transactions; and determining, by the processing device, possible resolutions for the patient credit balance accounts based on the identified criteria;

wherein each of the possible resolutions is associated with a resolvable error for a corresponding patient credit balance account which facilitates resolving the corresponding patient credit balance account, wherein one of the determined possible resolutions being an allowance error and wherein the allowance error is based on the identified criteria including accounts having duplicate adjustments, adjustments equal to the account balance, no payments in an account and adjustments in an account equaling an inverse of total charges of the account.

2. The method of claim 1 further comprising categorizing each patient credit balance account by determining a difficulty level in resolving that patient credit balance account by its determined possible resolution, each patient credit balance account is assigned a numeric value indicating its difficulty level in resolving.

3. The method of claim 1 wherein one of the criteria is duplicate payments associated with the patient credit balance account.

4. The method of claim 1 wherein one of the criteria is a payment equaling a balance of the patient credit balance account.

5. The method of claim 1 wherein one of the criteria is a payment being associated with the patient credit balance account.

6. The method of claim 1 wherein one of the criteria is only a single payment being associated with the patient credit balance account.

7. The method of claim 1 wherein one of the criteria being a patient payment being greater than or equal to an account balance.

8. The method of claim 1 wherein one of the criteria being matching credit and debit account balances being associated with the patient credit balance account.

9. The method of claim 1 wherein one of the criteria being an open debit account balance being associated with a same patient of the account.

10. The method of claim 1 wherein one of the determined possible resolutions being a patient overpayment.

11. The method of claim 10 wherein the patient overpayment criteria includes accounts having a patient payment greater than or equal to a balance of the account.

12. The method of claim 1 further comprising flagging the patient credit balance accounts when being identified as having Medicare payments.

13. The method of claim 12 wherein the identifying Medicare payments includes reviewing a service code or payments to determine whether the payment is a Medicare payment.

14. The method of claim 1 further comprising inputting, for use by the processing device, information associated with the credit balance accounts; wherein the step of identifying criteria is based on the inputted financial transactions and the inputted related accounts information.

15. The method of claim 1 further comprising outputting, by the processing device, the determined possible resolutions.

16. A method for determining a possible solution for a patient credit balance account, wherein the patient credit balance account is an account on a service provider's accounts receivable having financial transactions including cash payments and contractual allowances in excess of total charges and the patient credit balance accounts including information relating to services provided to a patient and accumulation of charges associated with the service, the method comprising:
   providing, for use by a processing device, a patient credit balance account and financial transaction information associated with the patient credit balance account;
   analyzing, by the processing device, the patient credit balance account and the financial transaction information to determine which criteria out of a set of criteria is associated with the patient credit balance account and the financial transaction information; and
   deciding, by the processing device, a possible resolution for the patient credit balance account based on the analyzed criteria, wherein the possible resolution is from a set of possible resolutions and one of the set of possible resolutions being an allowance error and
   wherein the allowance error is based on the determined criteria including accounts having duplicate adjustments, adjustments equal to the account balance, no payments in an account and adjustments in an account equaling an inverse of total charges of the account.

17. The method of claim 16 further comprising categorizing each patient credit balance account by determining a difficulty level in resolving that patient credit balance account by its determined possible resolution, each patient credit balance account is assigned a numeric value indicating its difficulty level in resolving.

18. The method of claim 16 wherein one of the set of criteria is duplicate payments associated with the patient credit balance account.

19. The method of claim 16 wherein one of the set of criteria is a payment equaling a balance of the patient credit balance account.

20. The method of claim 16 wherein one of the set of criteria is a payment being associated with the patient credit balance account.

21. The method of claim 16 wherein one of the set of criteria is only a single payment being associated with the patient credit balance account.

22. The method of claim 16 wherein one of the set of criteria being a patient payment being greater than or equal to an account balance.

23. The method of claim 16 wherein one of the set of criteria being matching credit and debit account balances being associated with the patient credit balance account.

24. The method of claim 16 wherein one of the set of criteria being an open debit account balance being associated with a same patient of the account.

25. The method of claim 16 wherein the possible solution is from a set of possible solutions and one of the set of possible solutions being a patient overpayment.

26. The method of claim 25 wherein the patient overpayment criteria includes accounts having a patient payment greater than or equal to a balance of the account.

27. The method of claim 16 further comprising flagging the patient credit balance account when being identified as having Medicare payments.

28. The method of claim 27 wherein the identifying Medicare payments includes reviewing a service code or payments to determine whether the payment is a Medicare payment.

29. The method of claim 16 further comprising providing, for use by the processing device, information associated with accounts related to the credit balance accounts; wherein the step of analyzing the patient credit balance accounts uses the inputted financial transactions and the inputted related accounts information.

30. The method of claim 16 further comprising outputting, by the processing device, the determined possible resolutions.

31. A system for determining possible resolutions of patient credit balance accounts, wherein patient credit balance accounts are accounts on a service provider's accounts receivable having financial transactions including cash payments and contractual allowances in excess of total charges and the patient credit balance accounts including information relating to services provided to a patient and accumulation of charges associated with the service, the system comprising:
   an input for receiving the patient credit balance accounts and financial transactions associated with the patient credit balance accounts; and
   a processing device and associated software for identifying criteria associated with possible resolutions to the patient credit balance accounts in response to the inputted financial transactions and for determining possible resolutions for the patient credit balance accounts based on the identified criteria;
   wherein each of the possible resolutions is associated with a resolvable error for a corresponding patient credit balance account which facilitates resolving the corresponding patient credit balance account,
   wherein one of the determined possible resolutions being an allowance error and wherein the processing device and associated software in evaluating the allowance error checks for the identified criteria including accounts having duplicate adjustments, adjustments equal to the account balance, no payments in an account and adjustments in an account equaling an inverse of total charges of the account.

32. The system of claim 31 wherein the processing device and associated software categorizes each patient credit balance account by determining a difficulty level in resolving that patient credit balance account by its determined possible resolution, each patient credit balance account is assigned a numeric value indicating its difficulty level in resolving.

33. The system of claim 31 wherein one of the criteria is duplicate payments associated with the patient credit balance account.

34. The system of claim 31 wherein one of the criteria is a payment equaling a balance of the patient credit balance account.

35. The system of claim 31 wherein one of the criteria is a payment being associated with the patient credit balance account.

36. The system of claim 31 wherein one of the criteria is only a single payment being associated with the patient credit balance account.

37. The system of claim 31 wherein one of the criteria being a patient payment being greater than or equal to an account balance.

38. The system of claim 31 wherein one of the criteria being matching credit and debit account balances being associated with the patient credit balance account.

39. The system of claim 31 wherein one of the criteria being an open debit account balance being associated with a same patient of the account.

40. The system of claim 31 wherein one of the determined possible resolutions being a patient overpayment.

41. The system of claim 40 wherein the processing device and associated software in evaluating the patient overpayment criteria checks for accounts having a patient payment greater than or equal to a balance of the account.

42. The system of claim 31 wherein the processing device and associated software flags the patient credit balance accounts when being identified as having Medicare payments.

43. The system of claim 42 wherein the processing device and associated software identifies the Medicare payments by reviewing a service code or payments to determine whether the payment is a Medicare payment.

44. The system of claim 31 wherein the input is configured to receive information associated with the credit balance accounts; wherein the identifying criteria is based on the inputted financial transactions and the inputted related accounts information.

45. The system of claim 31 wherein the processing device and associated software outputs the determined possible resolutions.

46. A system for determining a possible resolution for a patient credit balance account, wherein the patient credit balance account is an account on a service provider's accounts receivable having financial transactions including cash payments and contractual allowances in excess of total charges and the patient credit balance accounts including information relating to services provided to a patient and accumulation of charges associated with the service, the system comprising:
an input for receiving a patient credit balance account and financial transaction information associated with the patient credit balance account; and
the server device and associated software for analyzing the patient credit balance account and the financial transaction information to determine which criteria out of a set of criteria is associated with possible resolutions to the patient credit balance account and the financial transaction information and deciding a possible resolution for the patient credit balance account based on the analyzed criteria,
wherein one of the decided possible resolutions being an allowance error and wherein the server device and associated software in evaluating the allowance error checks for analyzed criteria including at least one of accounts having duplicate adjustments, adjustments equal to the account balance, no payments in an account and adjustments in an account equaling an inverse of total charges of the account.

47. The system of claim 46 wherein the server device and associated software categorizes each patient credit balance account by determining a difficulty level in resolving that patient credit balance account by its decided possible resolution, each patient credit balance account is assigned a numeric value indicating its difficulty level in resolving.

48. The system of claim 46 wherein one of the criteria is duplicate payments associated with the patient credit balance account.

49. The system of claim 46 wherein one of the criteria is a payment equaling a balance of the patient credit balance account.

50. The system of claim 46 wherein one of the criteria is a payment being associated with the patient credit balance account.

51. The system of claim 46 wherein one of the criteria is only a single payment being associated with the patient credit balance account.

52. The system of claim 46 wherein one of the criteria being a patient payment being greater than or equal to an account balance.

53. The system of claim 46 wherein one of the criteria being matching credit and debit account balances being associated with the patient credit balance account.

54. The system of claim 46 wherein one of the criteria being an open debit account balance being associated with a same patient of the account.

55. The system of claim 46 wherein one of the decided possible resolutions being a patient overpayment.

56. The system of claim 55 wherein the server device and associated software in evaluating the patient overpayment criteria checks for accounts having a patient payment greater than or equal to a balance of the account.

57. The system of claim 46 wherein the server device and associated software flags the patient credit balance accounts when being identified as having Medicare payments.

58. The system of claim 57 wherein the server device and associated software identifies the Medicare payments by reviewing a service code or payments to determine whether the payment is a Medicare payment.

59. The system of claim 46 wherein the input is configured to receive information associated with the credit balance accounts; wherein the analyzing the patient credit balance accounts is based on the inputted financial transactions and the inputted related accounts information.

60. The system of claim 46 wherein the server device and associated software outputs the decided possible resolutions.

\* \* \* \* \*